(12) United States Patent
Sekiya et al.

(10) Patent No.: US 8,975,575 B2
(45) Date of Patent: Mar. 10, 2015

(54) MASS SPECTROMETER AND MASS SPECTROMETRIC METHOD

(75) Inventors: Sadanori Sekiya, Shiga (JP); Masaki Murase, Aichi (JP); Hidenori Takahashi, Kyoto (JP); Kentaro Morimoto, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 14/009,587

(22) PCT Filed: Apr. 4, 2012

(86) PCT No.: PCT/JP2012/059162
§ 371 (c)(1),
(2), (4) Date: Dec. 27, 2013

(87) PCT Pub. No.: WO2012/137806
PCT Pub. Date: Oct. 11, 2012

(65) Prior Publication Data
US 2014/0224973 A1    Aug. 14, 2014

(30) Foreign Application Priority Data
Apr. 4, 2011  (JP) ................ 2011-082404

(51) Int. Cl.
*H01J 49/00*   (2006.01)
*H01J 49/26*   (2006.01)
(Continued)

(52) U.S. Cl.
CPC ............. *H01J 49/005* (2013.01); *H01J 49/004* (2013.01); *H01J 49/0481* (2013.01);
(Continued)

(58) Field of Classification Search
CPC ... H01J 49/004; H01J 49/0045; H01J 49/005; H01J 49/0036; H01J 49/0027; H01J 49/0481; H01J 49/26
USPC ............................................. 250/282, 281
See application file for complete search history.

(56) References Cited

U.S. PATENT DOCUMENTS 5,073,713 A * 12/1991 Smith et al. ............ 250/282
7,183,541 B2 * 2/2007 Iwamoto .................. 250/287
(Continued)

FOREIGN PATENT DOCUMENTS

CA   2 340 150 A1   12/2001
EP   1 220 290 A2    7/2002
(Continued)

OTHER PUBLICATIONS

Sadanori Sekiya, et al. "Glycan Analysis by Mass Spectrometry", Trends in Glycoscience and Glycotechnology, Jan. 2008, pp. 51-65, vol. 20, No. 111.
(Continued)

*Primary Examiner* — Nicole Ippolito
*Assistant Examiner* — Wyatt Stoffa
(74) *Attorney, Agent, or Firm* — Sughrue Mion, PLLC

(57) ABSTRACT

A mass spectrometry using helium as cooling gas is performed to obtain a first mass spectrum (S1), and another mass spectrometry using argon, which is heavier than helium, as cooling gas is performed to obtain a second mass spectrum for the same sample (S2). Due to the difference between the two gases in terms of the effect of promoting dissociation of modifications, an ion peak originating from a target compound from which all the modifications have been dissociated will appear with a higher intensity on the second mass spectrum. The peak patterns of the two mass spectra are compared to locate the all-dissociated ion peak while excluding unnecessary peaks (S3). Based on that peak, the assignment of each peak is determined (S4). Such a method is effective for enhancing the accuracy of the determination of the assignment of the peaks on the mass spectra and for improving the accuracy of identification or structural analysis in the case of a mass spectrometry of a compound to which an easily dissociable modification, such as a Sialylated glycosylated peptide, is bonded.

9 Claims, 11 Drawing Sheets

(51) Int. Cl.
  *H01J 49/04* (2006.01)
  *G01N 33/68* (2006.01)
(52) U.S. Cl.
  CPC ............ *H01J 49/0027* (2013.01); *H01J 49/26* (2013.01); *H01J 49/0045* (2013.01); *G01N 33/68* (2013.01); *G01N 33/6848* (2013.01); *G01N 2333/4728* (2013.01)
  USPC .......................................... 250/282; 250/281

(56) References Cited

U.S. PATENT DOCUMENTS

| | | | | |
|---|---|---|---|---|
| 2001/0052569 | A1* | 12/2001 | Bateman et al. | 250/288 |
| 2005/0189487 | A1* | 9/2005 | Iwamoto | 250/288 |
| 2010/0116982 | A1* | 5/2010 | Iwamoto et al. | 250/292 |
| 2011/0095180 | A1* | 4/2011 | Taniguchi | 250/287 |
| 2011/0215237 | A1* | 9/2011 | Bateman | 250/282 |
| 2014/0048701 | A1* | 2/2014 | Green et al. | 250/282 |
| 2014/0231642 | A1* | 8/2014 | Bateman | 250/282 |

FOREIGN PATENT DOCUMENTS

| | | |
|---|---|---|
| GB | 2 363 249 A | 12/2001 |
| JP | 2002-110081 A | 4/2002 |
| JP | 2005-243426 A | 9/2005 |
| JP | 2010-256101 A | 11/2010 |

OTHER PUBLICATIONS

Hong Wang, et al., "Integrated mass spectrometry-based analysis of plasma glycoproteins and their glycan modifications", Nature Protocols, 2011, Nature Protocols, 2011, pp. 253-269, vol. 6, No. 3.
Written Opinion of the International Searching Authority for PCT/JP2012/059162 dated Jun. 19, 2012.
International Preliminary Report on Patentability for PCT/JP2012/059162 dated Oct. 8, 2013.

* cited by examiner

54-RPTGEVYDIEIDTLETTCHVLDPTPLANCSVR-85

◆ : SIALIC ACID (Sia)
○ : GALACTOSE
■ : N-ACETYL GLUCOSAMINE
⊗ : MANNOSE

Ⓟ : PHOSPHATE ACID

FQSEEQQQTEDELQDK

127-LCPDCPLLAPLNDSR-141

◆ : SIALIC ACID (Sia)
○ : GALACTOSE
■ : N-ACETYL GLUCOSAMINE
⊗ : MANNOSE

Fig. 8
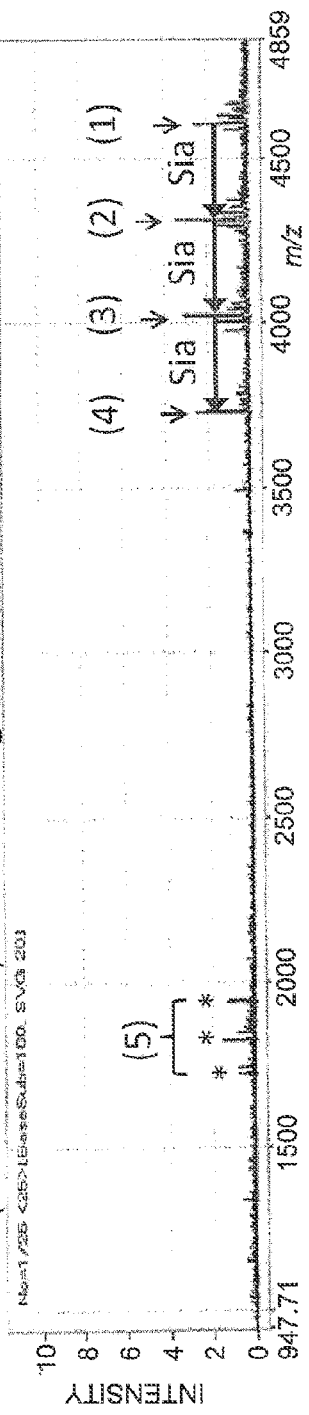
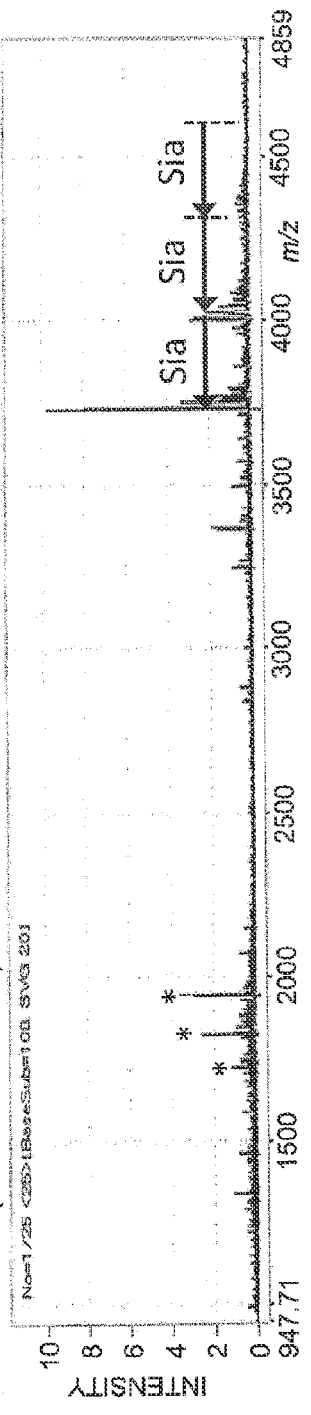
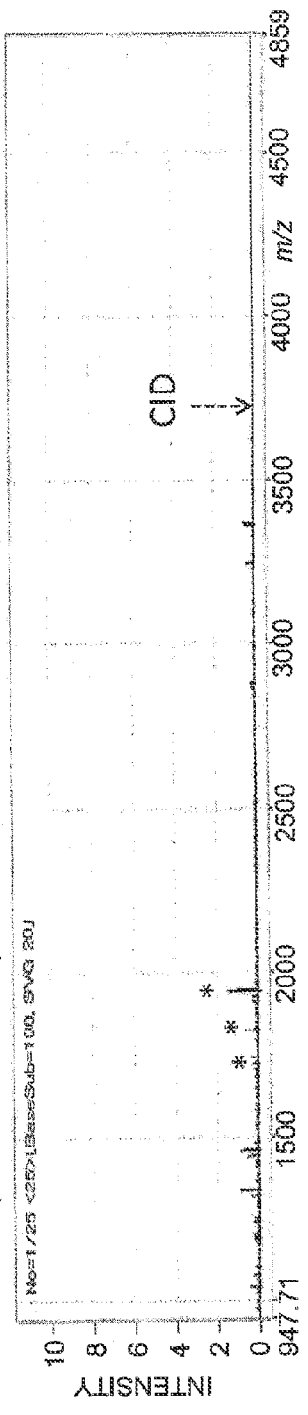

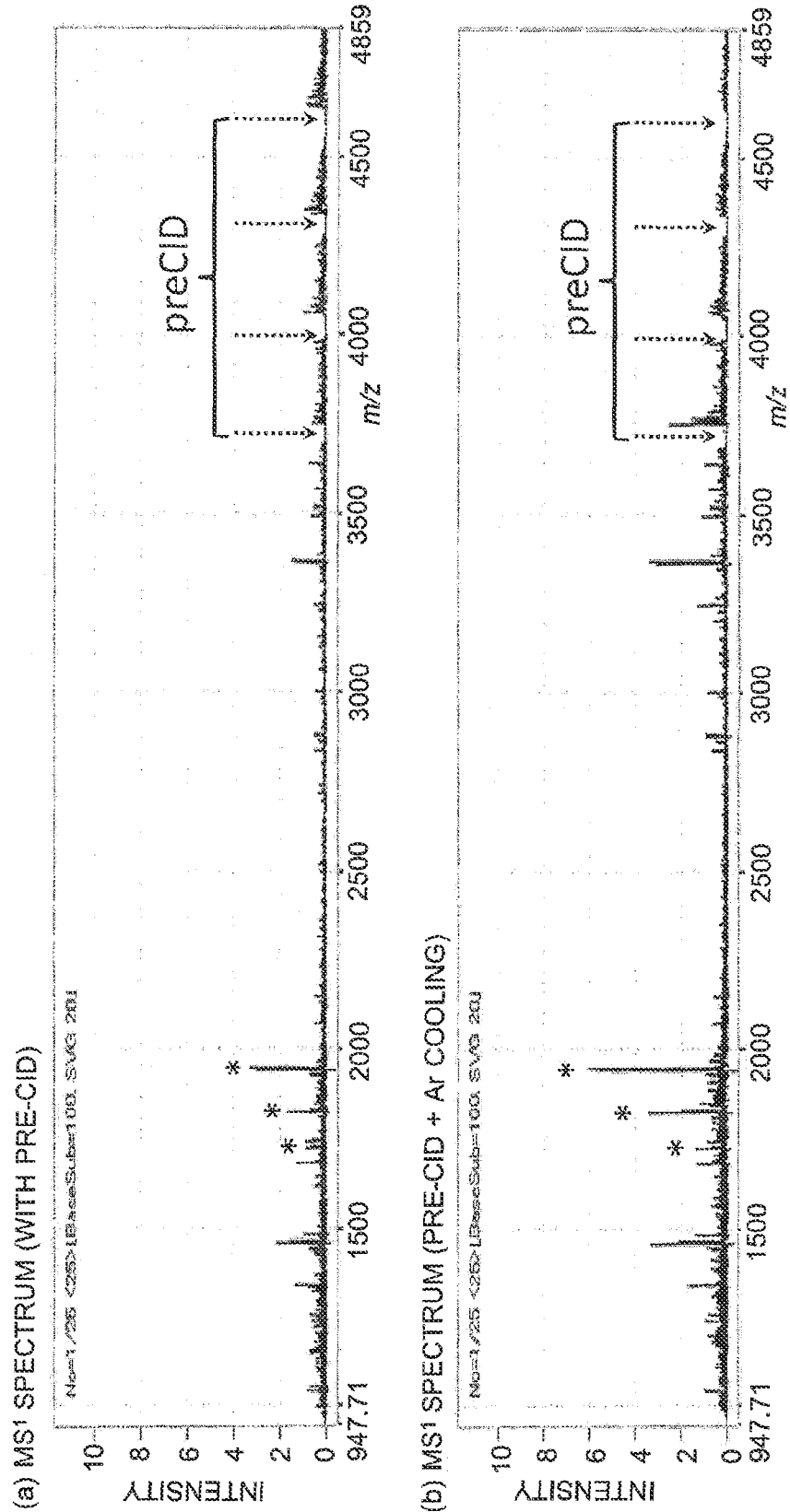

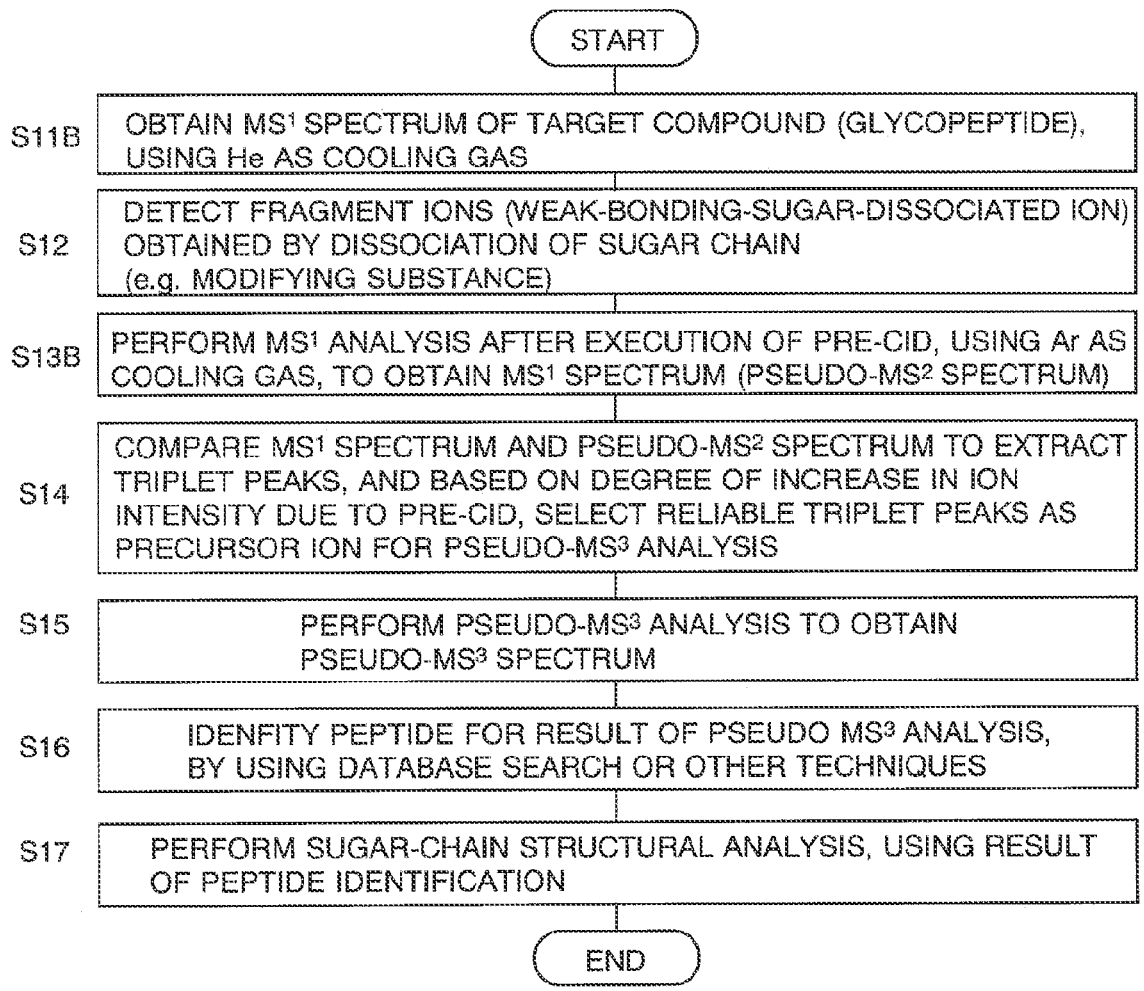

SEQUENCE LISTING

```
<160> NUMBER OF SEQ ID NOS: 3

<210> SEQ ID NO 1
<211> LENGTH: 32
<212> TYPE: PRT
<213> ORGANISM: Artificial Sequence
<220> FEATURE:
<223> OTHER INFORMATION: Synthetic peptide

<400> SEQUENCE: 1

Arg Pro Thr Gly Glu Val Tyr Asp Ile Glu Ile Asp Thr Leu Glu Thr
1               5                   10                  15

Thr Cys His Val Leu Asp Pro Thr Pro Leu Ala Asn Cys Ser Val Arg
            20                  25                  30

<210> SEQ ID NO 2
<211> LENGTH: 16
<212> TYPE: PRT
<213> ORGANISM: Artificial Sequence
<220> FEATURE:
<223> OTHER INFORMATION: Synthetic peptide

<400> SEQUENCE: 2

Phe Gln Ser Glu Glu Gln Gln Gln Thr Glu Asp Glu Leu Gln Asp Lys
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Synthetic peptide

<400> SEQUENCE: 3

Leu Cys Pro Asp Cys Pro Leu Leu Ala Pro Leu Asn Asp Ser Arg
1               5                   10                  15
```

MASS SPECTROMETER AND MASS SPECTROMETRIC METHOD

CROSS REFERENCE TO RELATED APPLICATIONS

This application is a National Stage of International Application No. PCT/JP2012/059162, filed on Apr. 4, 2012, which claims priority from Japanese Patent Application No. 2011-082404, filed on Apr. 4, 2011 the contents of all of which are incorporated herein by reference in their entirety.

TECHNICAL FIELD

The present invention relates to a mass spectrometer and a mass spectrometric method, and more specifically, to a mass spectrometer and a mass spectrometric method useful for the structural analysis of high molecular compounds, such glycopeptides.

BACKGROUND ART

For the structural analysis of high molecular compounds, such as sugar chains or peptides, an ion trap mass spectrometer including a MALDI (matrix-assisted laser desorption ionization) ion source and a three-dimensional quadrupole ion trap has been widely used. There are two types of systems for performing a mass spectrometry of various kinds of ions temporarily held in an ion trap; one type uses the mass-separating function of the ion trap itself, while the other type ejects ions from the ion trap and detects those ions after separating them according to their masses by a time-of-flight mass spectrometer provided outside the ion trap. In the following description, the two types of systems are collectively referred to as an ion trap mass spectrometer.

A generally used analytical technique for high molecular compounds by an ion trap mass spectrometer is as follows.

After various kinds of ions obtained by ionizing a target compound by a MALDI method are captured in an ion trap, an ion-selecting operation is performed in such a manner that a kind of ion having a specific mass-to-charge ratio m/z is selectively retained as a precursor ion within the ion trap, while the other kinds of ions are ejected to the outside of the ion trap. Subsequently, a collision-induced dissociation (CID) gas is introduced into the ion trap, and the precursor ion is excited to make it collide with the CID gas and promote its dissociation. If the target structure cannot be adequately dissociated by a single CID operation, the selection of the precursor ion and the CID operation may be repeated a plurality of times. As a result of the CID operation thus performed one or more times for ions originating from the compound to be analyzed, a number of finely fragmented product ions are obtained, which are subsequently subjected to an ion-detecting process with a mass scan to obtain an $MS^n$ spectrum. By analyzing this $MS^n$ spectrum, the structure of the target compound is deduced.

In general, in an ion trap mass spectrometer, an operation called the "cooling" is performed in order to gather captured ions around the center of the capturing space of the ion trap for the purpose of improving the detection sensitivity and the mass-resolving power. That is to say, a cooling gas, which is an inert gas such as helium (He), is introduced into the ion trap and the captured ions are made to come in contact with the cooling gas so as to lower the kinetic energy of the ions. The ions having the kinetic energy thus decreased are more easily affected by the capturing electric field. Therefore, they do not widely spread within the capturing space but are more likely to gather around the center of the capturing space. In the case of the previously described sequential processes for the mass spectrometry, the cooling is normally performed after the ions are introduced into the ion trap from outside. The cooling is also performed after a precursor ion is dissociated by the CID operation and the thereby produced product ions are captured by the capturing electric field.

It is often the case that a high molecular compound to be analyzed by the previously described ion trap mass spectrometer includes a modification or functional group that easily dissociates Typical examples of such modifications or functional groups include sialic acids, sulfate groups and phosphate groups. It is commonly known that, when a sugar chain to which sialic acid is bonded (which is a kind of acidic sugar), or a glycopeptide to which a sialic-acid-bonded sugar chain is added, is dissociated by a low-energy CID in an ion trap mass spectrometer using a MALDI ion source, the sialic acid is preferentially dissociated.

However, the dissociation of sialic acid easily occurs not only in the CID process; it can also easily occur due to an in-source decay or a collision with the cooling gas, as well as due to a post-source decay if a time-of-flight mass spectrometer is used. Therefore, peaks of ions produced by a partial or entire dissociation of sialic acids are also observed even in a normal mass spectrometry in which no CID operation is performed (see Non-Patent Document 1 or other documents). Thus, particularly in the case of an ion trap mass spectrometer using a MALDI ion source, there is the problem that, if a compound to which an easily dissociable modification like the aforementioned ones is bonded is contained in the unknown sample, both the peaks of ions from which the modification has been dissociated and the peaks of ions from which the modification has not been dissociated will appear in the mass spectrum, making it difficult to determine the assignment of the ion peaks.

Furthermore, in the case where the assignment of the peaks is determined based on the mass-to-charge-ratio difference between each pair of the peaks in a mass spectrum obtained by a mass spectrometry of a target compound to which the aforementioned modification is bonded, if there is a peak which is unrelated with the target compound and yet has a mass-to-charge ratio that accidentally coincides with that of the dissociated modification (e.g. an impurity peak or noise peak), the assignment of that peak will be incorrectly determined, making the identification of the target compound difficult or incorrect.

In the case where the identification or structural analysis of an N-linked glycopeptide is performed by using an ion trap mass spectrometer, the following problem also exists: An $MS^2$ spectrum obtained for an N-linked glycopeptide has three characteristic peaks appearing at predetermined intervals of mass-to-charge ratio (which are hereinafter called the "triplet peaks"), which specifically includes a peptide ion resulting from complete dissociation of sugar, a $^{0,2}X(83Da)$-added peptide ion resulting from a cross-ring cleavage of the HexNAc sugar, and a HexNAc(203Da)-added peptide ion arranged in ascending order of mass-to-charge ratio. Therefore, the $MS^2$ spectrum normally is initially analyzed for the neutral losses of the sugar to locate triplet peaks, after which an $MS^3$ analysis with an ion corresponding to these peaks designated as the precursor ion is performed. Then, based on the thereby obtained $MS^3$ spectrum, the peptide and the glycosylation site are identified.

In general, since the amount of ions detected in an $MS^2$ analysis is smaller than in the normal mass spectrometry ($MS^1$ analysis) in which no CID operation is performed, it is necessary to increase the number of signal accumulations so as to create an MS² spectrum with adequate strength, which means that the MS² analysis must be repeated an accordingly large number of times. As a result, a long period of time is required to identify a peptide, and in the case of an analysis of a trace amount of sample originating from a living body, the sample may possibly be exhausted in the middle of the analysis, making it impossible to identify a peptide. Furthermore, in the case where 2,5-dihydroxybenzoic acid (DHB), which is recognized to be suitable for the ionization of glycopeptides in the MALDI method, is used as the matrix, it is known that the matrix sublimates during an analysis in vacuum atmosphere, terminating the ionization of the sample (i.e. the peptide). Thus, it has been a major problem for an analysis of N-linked glycopeptides to shorten the period of time required for the identification of a peptide.

BACKGROUND ART DOCUMENT

Patent Document

Patent Document 1: JP-A 2005-243426

Non-Patent Document

Non-Patent Document 1: Sekiya and Iida, "Glycan Analysis by Mass Spectrometry", *Trends in Glycoscience and Glycotechnology*, Vol. 20, No. 111, January 2008, pp. 51-65

SUMMARY OF THE INVENTION

Problem to be Solved by the Invention

The present invention has been developed in view of the previously described problems, and its primary objective is to provide a mass spectrometer and a mass spectrometric method by which the assignment of peaks originating from a target compound and appearing on a mass spectrum can be determined with high accuracy in a structural analysis of a high molecular compound containing an easily dissociable modification or functional group.

The secondary objective of the present invention is to provide a mass spectrometer and a mass spectrometric method which can identify peptides constituting a glycopeptide while reducing the number of signal accumulations and hence the analyzing time as compared with conventional methods.

Means for Solving the Problem

As already noted, easily dissociable modifications or functional groups (such as sialic acids, sulfate groups and phosphate groups) will be easily dissociated in the process of an in-source decay or a post-source decay, during the cooling process in the ion trap or the like. For example, the cooling gas used in an ion trap mass spectrometer including a MALDI ion source should preferably be an inert gas with a low mass. Typically, helium is used. This is because, if a high-mass gas is used as the cooling gas, the dissociation of ions originating from the target compound easily occurs in the course of the cooling process, causing the aforementioned modifications or functional groups to be noticeably dissociated (see Patent Document 1 or other documents).

In general, such an unintended dissociation of the target compound in the cooling process should in itself be regarded as an undesirable phenomenon. However, the present inventors have directed their attention to the fact that the dissociating effect in the cooling process differs depending on the kind of cooling gas, and have conceived the idea of positively using this dissociating effect for the assignment of the peaks on a mass spectrum. They also have conceived the idea that a similar dissociating effect which occurs in a process other than the cooling can also be positively used for the assignment of the peaks on a mass spectrum by promoting the dissociation of a modification or the like included in the target compound by using that dissociating effect.

Thus, the first aspect of the present invention aimed at solving the previously described problems is a mass spectrometer including a mass analyzer for performing a mass spectrometry of ions originating from a compound to be analyzed and a detector for detecting the ions separated by the mass analyzer according to their mass-to-charge ratios, the mass spectrometer further including:

a) a non-ion-selecting fragmentation promoter for promoting fragmentation of the ions originating from a target compound without an ion-selecting operation;

b) a first analysis executer for obtaining a first mass spectrum by performing a mass spectrometry of the ions originating from the target compound by using the mass analyzer, without performing a fragmentation-promoting operation by the non-ion-selecting fragmentation promoter;

c) a second analysis executer for obtaining a second mass spectrum by performing a mass spectrometry of the ions originating from the target compound by using the mass analyzer after performing a fragmentation-promoting operation by the non-ion-selecting fragmentation promoter; and d) a data processor for determining an assignment of a peak originating from the target compound by comparing the first mass spectrum and the second mass spectrum.

The second aspect of the present invention aimed at solving the previously described problems is a mass spectrometric method using a mass spectrometer including a mass analyzer for performing a mass spectrometry of ions originating from a compound to be analyzed and a detector for detecting the ions separated by the mass analyzer according to their mass-to-charge ratios, the mass spectrometric method including:

a) a first analysis execution step in which a first mass spectrum is obtained by performing a mass spectrometry of the ions originating from the target compound by using the mass analyzer;

b) a second analysis execution step in which a second mass spectrum is obtained by performing a mass spectrometry of the ions originating from the target compound by using the mass analyzer after performing a non-ion-selecting fragmentation-promoting operation in which fragmentation of the ions is promoted without an ion-selecting operation; and c) a data-processing step in which an assignment of a peak originating from the target compound is determined by comparing the first mass spectrum and the second mass spectrum.

The mass spectrometer according to the first aspect of the present invention is a system for carrying out the mass spectrometric method according to the second aspect of the present invention. One typical form of the mass spectrometer according to the first aspect of the present invention is an ion trap mass spectrometer having an ion trap capable of capturing ions originating from a compound to be analyzed, in which the ions temporarily captured in the ion trap are either subjected to a mass spectrometry by the ion trap itself, or ejected from the ion trap and subjected to a mass spectrometry by an external mass analyzer.

In the first and second aspects of the present invention, one of the compounds to be analyzed is typically a compound having a core structure to which one or a plurality of weak-bonding modifications and/or functional groups are bonded and hence the modifications and/or functional groups easily dissociate in some process, such as the ionization process, the process of transporting ions from an external ion source into an ion trap or another ion optical element, or the cooling process within the ion trap. For example, the aforementioned sialic acid, sulfate group and phosphate group are specific examples of such modifications and/or functional groups.

In the case where a target component in which one or more weak-bonding substances (modifications or functional groups) are bonded to a core structure is contained in a sample, when the fragmentation-promoting operation by the non-ion-selecting fragmentation promoter is performed on the ions produced from that sample, the modifications and/or functional groups will noticeably be dissociated from the core structure. On the first mass spectrum which shows an analysis result obtained without performing the fragmentation-promoting operation by the non-ion-selecting fragmentation promoter, a peak or peaks originating from the target compound on which the modifications or functional groups still remain (in the bonded form) will appear with adequate intensities. By contrast, on the second mass spectrum showing an analysis result obtained by performing the fragmentation-promoting operation by the non-ion-selecting fragmentation promoter, the intensity of the peak or peaks originating from the target compound on which the modifications or functional groups still remain is significantly decreased, whereas a peak or peaks originating from the target compound with all the modified components or functional groups dissociated, i.e. the core structure of the target compound, will appear with high intensities.

Accordingly, in the mass spectrometer according to the first aspect of the present invention, the data processor may compare the peak pattern of the first mass spectrum with the peak pattern of the second mass spectrum and make at least a comparison of the intensities of the peaks at the same mass-to-charge ratio or a comparison of the intensity ratio of a plurality of peaks having a predetermined mass-to-charge-ratio difference on one of the mass spectra so as to locate a peak corresponding to the core structure of the target compound from which all the weak-bonding substances have been dissociated.

For example, a plurality of peaks appearing on the first mass spectrum at mass-to-charge-ratio intervals corresponding to a known kind of easily dissociable modification are extracted as a candidate group of the peaks of the dissociated ions, and the second mass spectrum is searched for a peak corresponding to the peak having the smallest mass-to-charge ratio in that candidate group. If no such peak is substantially present on the second mass spectrum, it is probable that the aforementioned peak having the smallest mass-to-charge ratio in the candidate group of the peaks of the dissociated ions on the first mass spectrum is not a peak originating from the target compound. Therefore, this peak is excluded from the first mass spectrum, and the degree of increase in the signal intensity due to the non-ion-selecting fragmentation-promoting operation is determined for a peak having the second smallest mass-to-charge ratio in the candidate group of the dissociated ion peaks. For the determination of this degree of increase, the intensity ratio of a plurality of peaks included in the candidate group of the dissociated ion peaks can be used.

If the degree of increase in the intensity is greater than a predetermined threshold, the peak can be regarded as a peak corresponding to the core structure having all the easily dissociable modifications dissociated. Conversely, if the degree of increase is equal to or less than the predetermined threshold, it is probable that the peak is not a peak corresponding to the core structure. In this manner, a peak corresponding to the core structure of the target compound is searched for, and based on the thereby located peak, a peak or peaks originating from the target compound from which a portion of the modifications have been dissociated (leaving the other portion of the modifications in the bonded form) are located, and the assignment of each peak is determined.

In the case where the compound to be analyzed is an N-linked glycopeptide, the aforementioned characteristic triplet peaks appear on the mass spectrum.

Accordingly, in the mass spectrometer according to the present invention, when the target compound is an N-linked glycopeptide, the data processor extracts triplet peaks characteristic of N-linked glycopeptides by comparing the first mass spectrum and the second mass spectrum, and the mass spectrometer further includes:

a pseudo-$MS^3$ analysis executer for performing an $MS^2$ analysis using the triplet peaks extracted by the data processor as a precursor ion, as a pseudo-$MS^3$ analysis, for the ions originating from the target compound; and a peptide identifier for identifying a peptide constituting the target compound based on a mass spectrum obtained by the pseudo-$MS^3$ analysis.

This analysis is given the name of "pseudo-$MS^3$ analysis" since this analysis can yield a result substantially similar to an $MS^3$ analysis even though it is nominally an $MS^2$ analysis in terms of the number of operations including the selection of a precursor ion paired with a CID operation.

As compared with the true $MS^3$ analysis, the pseudo-$MS^3$ analysis includes a smaller number of precursor-ion selecting operations and hence requires a shorter period of time for the analysis. The smaller number of precursor-ion selecting operations also means that the decrease in the amount of precursor ions which considerably occurs through the selection of the precursor ion is suppressed and a larger amount of ions is available for the detection, so that the number of signal accumulations can be reduced. Accordingly, the peptides constituting a glycopeptide can be identified in a shorter period of analyzing time and with a lower consumption of the sample.

The non-ion-selecting fragmentation promoter can have various configurations. As already noted, the kind of cooling gas used in the cooling process within the ion trap significantly affects the degree of ease of the dissociation of the modifications and/or functional groups included in the compound. For example, in the case where the sample contains a target compound with one or a plurality of easily dissociable modifications and/or functional groups bonded to a core structure, if the cooling is performed with helium as the cooling gas, a comparatively small amount of modifications or functional groups will be dissociated from the core structure in the cooling process. By contrast, if the cooling is performed with argon as the cooling gas, which has a larger mass than helium, the modifications and/or functional groups will noticeably be dissociated from the core structure in the cooling process.

Accordingly, the first mode of the mass spectrometer according to the first aspect of the present invention is configured as a mass spectrometer in which ions to be analyzed are temporarily captured in an inner space of an ion trap and then subjected to a mass spectrometry by the ion trap, or by an external mass analyzer after being ejected from the ion trap, wherein:

the non-ion-selecting fragmentation promoter introduces, into the ion trap, an inert gas having a comparatively strong dissociating effect as a cooling gas for cooling the ions captured in the inner space of the ion trap.

In a more specific configuration of this mass spectrometer:

the non-ion-selecting fragmentation promoter includes a gas-selecting supplier for selectively introducing, into the ion trap, either a first inert gas or a second inert gas having a stronger dissociating effect than the first inert gas;

the first analysis executer obtains the first mass spectrum by performing a mass spectrometry of the ions originating from the target compound after performing a cooling process in which the first inert gas selected by the gas-selecting supplier is used as the cooling gas; and the second analysis executer obtains the second mass spectrum by performing a mass spectrometry of the ions originating from the target compound after performing a cooling process in which the second inert gas selected by the gas-selecting supplier is used as the cooling gas.

The second inert gas has a larger mass than the first inert gas. The mass difference should preferably be as large as possible. In one preferable mode of the present invention, the first inert gas is helium, i.e. the lightest inert gas, while the second inert gas is nitrogen, neon, argon, krypton, xenon or a mixture of two or more of these gases. In terms of mass, it is preferable to use krypton, xenon or the like as the second inert gas. However, these kinds of gas are not only expensive but also lack versatility. Accordingly, in general, argon or nitrogen is appropriate as the second inert gas.

With the first mode of the present invention, it is possible to obtain a first mass spectrum in which the peaks originating from the target compound retaining modifications and/or functional groups occur with adequate intensities, and a second mass spectrum in which a peak or peaks originating from the core structure of the target compound from which all the modifications and functional groups have been dissociated occur with high intensity. Therefore, an analysis for assigning the peaks will be easy to perform.

The second mode of the mass spectrometer according to the first aspect of the present invention is configured as a mass spectrometer in which ions to be analyzed are temporarily captured in an inner space of an ion trap and then subjected to a mass spectrometry by the ion trap, or by an external mass analyzer after being ejected from the ion trap, wherein:

the non-ion-selecting fragmentation promoter performs a collision-induced dissociating operation without selecting a precursor ion while the ions originating from the target compound are captured within the ion trap.

The omission of the selection of the precursor ion before the collision-induced dissociating operation makes it unnecessary to provide the period of time for the selection of the precursor ion. Furthermore, the number of accumulations of the signal intensity can be decreased since there is no reduction in the amount of ions due to the selection of the precursor ion. Accordingly, the peptides constituting a glycopeptide can be identified in a shorter period of analyzing time and with a lower consumption of the sample.

It is naturally possible to use both the first and second modes of the present invention. That is to say, the non-ion-selecting fragmentation promoter may be configured so that it introduces, into the ion trap, an inert gas having a comparatively strong dissociating effect as the cooling gas, and furthermore, performs a collision-induced dissociating operation without selecting a precursor ion while the ions originating from the target compound are captured within the ion trap. Such a system exhibits an even stronger dissociation-promoting effect and facilitates the peak assignment, making it possible to shorten the analyzing time, or alternatively, to perform the measurement with approximately the same number of data accumulations as in the conventional cases and thereby improve the identifying performance based on a pseudo-$MS^3$ analysis or the like of the assigned peaks.

Although there are various techniques for producing ions to be analyzed, the dissociation of modifications and/or functional components from the ions originating from the target component is particularly easy to occur in the case where a target compound is ionized by a MALDI ion source and the produced ions are captured into and cooled within an ion trap. Accordingly, the mass spectrometer and the mass spectrometric method according to the present invention are particularly useful for an ion trap mass spectrometer using a MALDI ion source and for a mass spectrometric method using such a mass spectrometer.

Effect of the Invention

With the mass spectrometer and the mass spectrometric method according to the present invention, when a mass spectrometry is performed for a compound having one or more easily dissociable modifications and/or functional groups bonded to a core structure, the assignment of the peaks originating from a compound from which the modifications and/or functional groups have been partially or entirely dissociated, or the peaks originating from a compound from which no modification or functional group has been dissociated, can be determined with high accuracy and reliability. Therefore, when the target compound is of an unknown kind, the compound can be identified with higher accuracy and its structure can be more easily analyzed.

As compared to conventional techniques, the mass spectrometer and the mass spectrometric method according to the present invention can identify peptides constituting a glycopeptide with a smaller number of analyses and a smaller number of signal accumulations. Therefore, the analyzing time will be shortened, and the sample consumption will be reduced. Thus, a high-accuracy structural analysis of glycopeptides can be performed with a smaller amount of sample than in conventional cases.

Furthermore, if peptides constituting a glycopeptide are identified by the mass spectrometer and the mass spectrometric method according to the present invention before a sugar-chain structural analysis of the glycopeptide is performed, it is possible to use the sugar-chain database search software introduced in the document (*Nature Protocols*, 2011, 6(3), pp. 253-269) to identify the sugar-chain structure. This enables identification of the sugar-chain structure using known glycopeptide information even if the number of fragment ions located on the mass spectrum is too small to obtain a useful result by de novo sequencing, a technique which has been frequently used for a neutral-loss analysis.

BRIEF DESCRIPTION OF THE DRAWINGS

FIG. 6 shows mass spectra obtained by actual measurements of the glycopeptide shown in

FIG. 3.

FIG. 8 shows mass spectra and an $MS^2$ mass spectrum obtained by actual measurements of the glycopeptide shown in FIG. 5.

FIG. 13 shows (a) an $MS^1$ spectrum obtained by an actual measurement of the glycopeptide shown in FIG. 5 in which a pre-CID was performed, and (b) an $MS^1$ spectrum obtained by an actual measurement of the same glycopeptide in which argon was used as the cooling gas and the pre-CID was performed.

FIG. 14 is a flowchart showing the process steps of a glycopeptide structural analysis by the ion trap mass spectrometer of the second embodiment in which argon is used as the cooling gas.

MODE FOR CARRYING OUT THE INVENTION

[First Embodiment]

An ion trap mass spectrometer as the first embodiment of the present invention, and a characteristic mass spectrometric method performed by the mass spectrometer, are hereinafter described with reference to the attached drawings.

Figure 1:
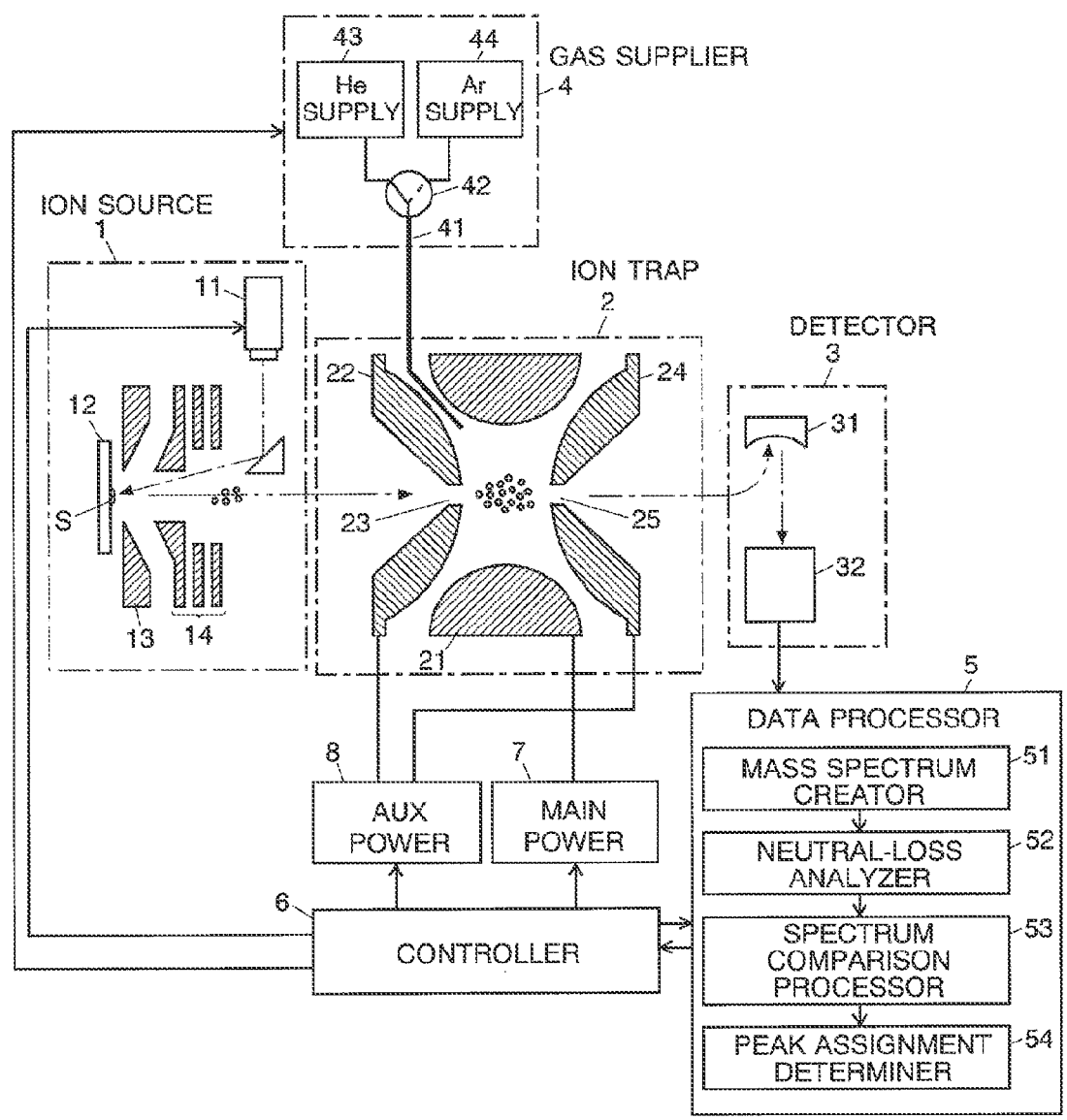
FIG. 1 is an overall configuration diagram of an ion trap mass spectrometer as the first embodiment of the present invention.

FIG. 1 is an overall configuration diagram of the ion trap mass spectrometer of the first embodiment. This ion trap mass spectrometer includes an ion source 1 for ionizing a target sample, a three-dimensional quadrupole ion trap 2 for holding ions and for separating them according to their mass-to-charge ratios, and a detector 3 for detecting the ions.

The ion source 1, which is a MALDI ion source using a MALDI method, includes a laser irradiation unit 1 for emitting a pulsed laser light, a sample plate 12 to which a sample S containing a target compound is attached, an aperture 13 for drawing ions released from the sample S by irradiation with the laser light and for limiting the drawing direction, and an ion lens 14 for guiding the drawn ions, and other components.

The ion trap 2 includes one ring-shaped electrode 21, an entrance end-cap electrode 22 and an exit end-cap electrode 24, the two end-cap electrodes facing each other across the ring electrode 21. The space surrounded by these three electrodes 21, 22 and 24 functions as the capturing space. An ion injection hole 23 is bored almost at the center of the entrance end-cap electrode 22. Ions ejected from the ion source 1 are introduced through this ion injection hole 23 into the ion trap 2. On the other hand, an ion ejection hole 25 is bored almost at the center of the exit end-cap electrode 22. Ions ejected from the ion trap 2 through this ion ejection hole 25 arrive at and are detected by the detector 3. Furthermore, the ion trap 2 is provided with a gas supplier 4 including a gas introduction tube 41, a gas selection valve 42, a helium supply source 43, an argon supply source 44, and other components.

The detector 3, which includes a conversion dynode 31 for converting ions into electrons and a secondary electron multiplier 32 for amplifying and detecting the electrons coming from the conversion dynode 31, produces a detection signal corresponding to the amount of incident ions and sends the signal to a data processor 5. The data processor 5 includes various functional blocks, such as a mass spectrum creator 51 (which creates a mass spectrum based on the detection signals obtained with the detector 3 for ions which are mass-separated and sequentially discharged from the ion trap 2), a neutral-loss analyzer 52 (which performs a characteristic data processing), a spectrum comparison processor 53 and a peak assignment determiner 54.

Under the control of a controller 6, a main power source 7 applies an ion-capturing rectangular voltage to the ring electrode 21 of the ion trap 2. For example, the ion-capturing rectangular voltage has an amplitude within a range of ±100 to ±1000 V, and its frequency f is normally within a range from several tens of kHz to several MHz. An auxiliary power source 8 applies a different rectangular low voltage to each of the end-cap electrodes 22 and 24 so as to cause resonance oscillation of ions captured in the ion trap 2 in the process of low-energy CID or to discharge ions from the ion trap 2.

The controller 6 also has the function of controlling the laser irradiation unit 11, the gas selection valve 42, the data processor 5 and other components in addition to the main power source 7 and the auxiliary power source 8. Furthermore, the controller 6 is provided with a measurement sequence (i.e. a procedure for performing an analysis) in the form of a control program. In the mass spectrometer of the first embodiment, a characteristic measurement sequence for carrying out the mass spectrometric method (which will be described later) is included as a part of the control program. The controller 6 and the data processor 5 can be configured so as to carry out the functions to be described later by executing a dedicated processing and controlling software program installed beforehand in a personal computer.

Figure 2:
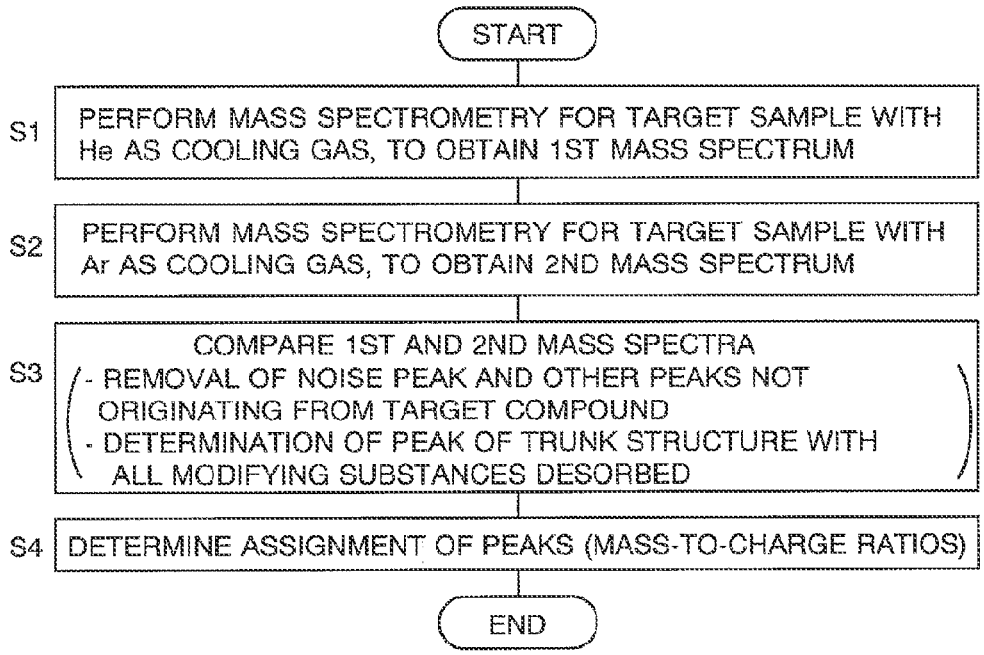
FIG. 2 is a flowchart showing the process steps of a characteristic analyzing operation using the ion trap mass spectrometer of the first embodiment.

When an unknown kind of high molecular compound including a modification or functional group which is easy to dissociate (which is weak-bonding) is to be analyzed by using the ion trap mass spectrometer of the first embodiment, an operator performs a predetermined operation on an input unit (not shown), whereupon a characteristic analysis is performed according to the processes shown by the flowchart of FIG. 2. Examples of the easily dissociable modifications and functional groups include sulfate groups and phosphate groups in addition to sialic acids. Representative examples of the compounds to be analyzed are sialic-acid-bonded sugar chains, glycopeptides to which a sialic-acid-bonded sugar chain is added, sulfated sugar chains, sulfated peptides, phosphorylated sugar chains, and phosphorylated peptides. The following description takes the example of analyzing a fetuine glycopeptide (bovine fetuine-GP3) having the structure shown in FIG. 3. As shown, this glycopeptide has three sialic acids bonded to a terminal of a core structure.

When the analysis is initiated, a mass spectrometry for the target sample is initially performed under the condition that helium is used as the cooling gas, and a mass spectrum is created based on the data obtained by the analysis (Step S1). A more specific description is as follows: Under the control of the controller 6, the laser irradiation unit 11 emits a laser light for a short period of time. The laser light is irradiated onto the (target) sample S, whereby the matrix in the sample S is rapidly heated, turning into gas together with the target compound. During this process, the target compound is ionized. Almost simultaneously with or earlier than that, the gas supplier 4 is operated so that the helium from the helium supply source 43 is selected by the gas selection valve 42 and supplied through the gas introduction tube 41 into the ion trap 2.

The ions generated by the laser irradiation are focused by an electrostatic field formed by the ion lens 14, to be introduced through the ion entrance hole 23 into the ion trap 2. Due to a radio-frequency electric field formed according to the ion-capturing rectangular voltage applied from the main power source 7, the ions are captured within the inner space of the ion trap 2, where they come in contact with the helium introduced as the cooling gas. Thus, the ions are cooled.

Figure 3:
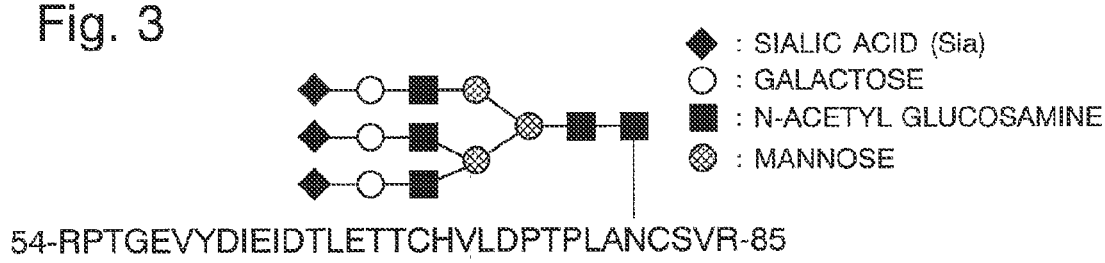
FIG. 3 shows a schematic structure of a glycopeptide (SEQ ID NO: 1) as one example of the analysis target.

Since the sialic acids bonded to the glycopeptide having the structure shown in FIG. 3 are easy to dissociate, a portion of the sialic acids dissociate during the ionization or while the ions are transported from the ion source 1 to the ion trap 2. Another portion of the sialic acids also dissociates due to the contact of the ions with helium during the cooling process. However, helium has a small mass and its dissociation-promoting effect is not very strong. Therefore, four kinds of ions originating from the target compound will primarily be captured in the ion trap 2: $[M+H]^+$, an ion originating from the target compound with no dissociation of sialic acids; $[M+H]^+$-Sia, an ion originating from the target compound with one sialic acid dissociated; $[M+H]^+$-2Sia, an ion originating from the target compound with two sialic acids dissociated; and $[M+H]^+$-3Sia, an ion originating from the target compound with three (all) sialic acids dissociated.

Figure 6:
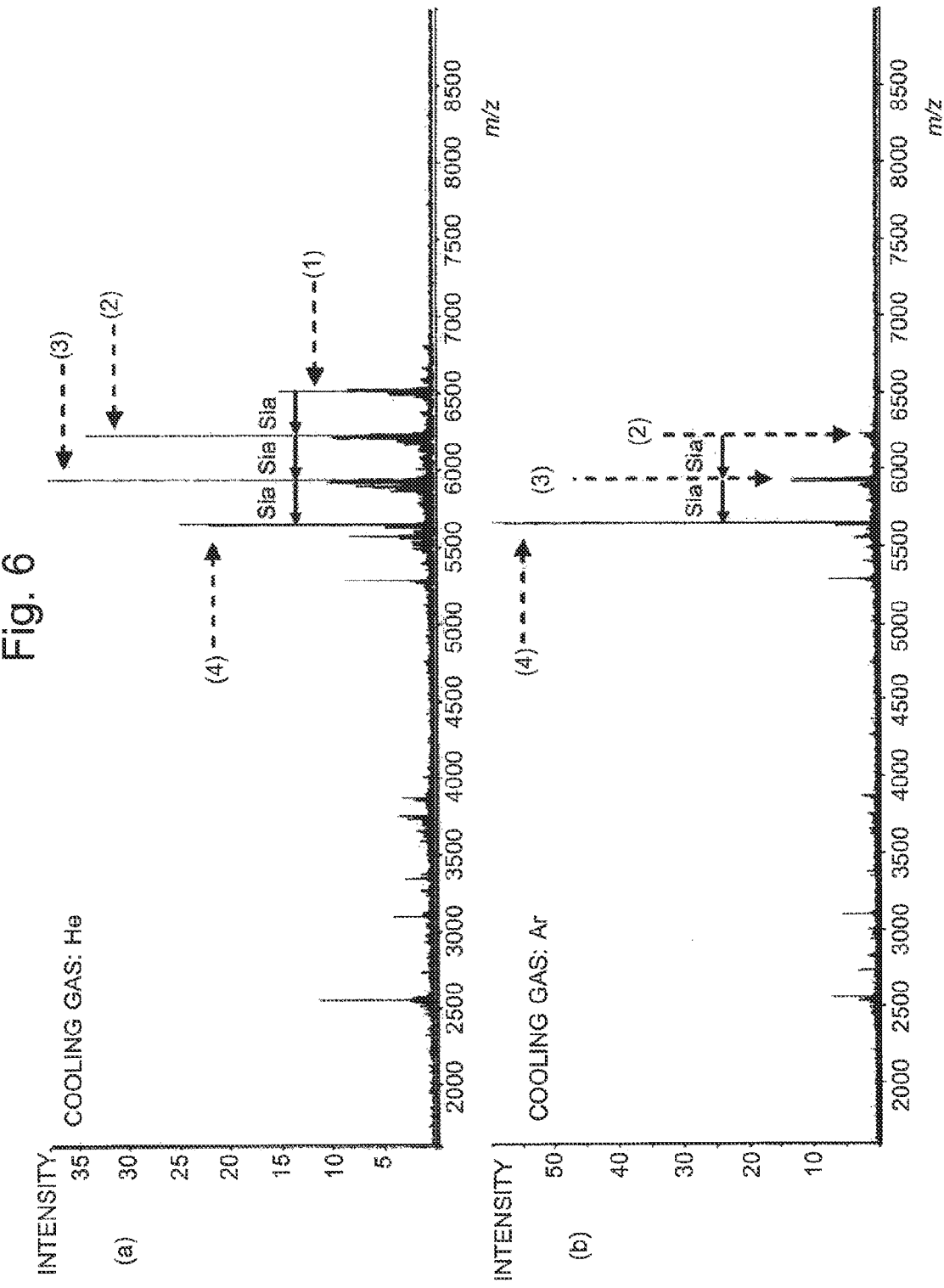

After the ions are gathered around the center of the capturing space by performing the cooling for a predetermined period of time, the controller 6 controls the voltages applied from the main power source 7 and the auxiliary power source 8 to the electrodes 21, 22 and 24 so that the ions having different mass-to-charge ratios are sequentially ejected from the ion trap 2. The ion-intensity signal produced by the detector 3 along with such a mass scan are sent to the data processor 5, in which the mass spectrum creator 51 creates a mass spectrum covering a predetermined range of mass-to-charge ratios. FIG. 6(a) is one example of the mass spectrum obtained by an actual measurement with helium as the cooling gas. DHB was used as the matrix in the measurement. In FIG. 6(a), the peaks (1), (2), (3) and (4) respectively correspond to $[M+H]^+$, $[M+H]^+$-Sia, $[M+H]^+$-2Sia and $[M+H]^+$-3Sia, although the assignment of these peaks is unknown when the target compound remains unidentified.

Next, a mass spectrometry for the same target sample is performed under the condition that argon is used as the cooling gas, and a mass spectrum is created based on the data obtained by the analysis (Step S2). The analyzing conditions in this step are the same as in Step S1 except for the operation of the gas supplier 4 in which the argon from the argon supply source 44 is selected by the gas selection valve 42 and supplied through the gas introduction tube 41 into the ion trap 2.

In the present analysis, as in the analysis of Step S1, a portion of the sialic acids are dissociated during the ionization or while ions are transported from the ion source 1 to the ion trap 2. On the other hand, the argon introduced as the cooling gas into the ion trap 2 has a much larger mass than helium and hence an accordingly stronger effect for promoting the dissociation or fragmentation of the modifications. Therefore, the dissociation of sialic acids noticeably occurs from the $[M+H]^+$, $[M+H]^+$-Sia and $[M+H]^+$-2Sia ions all of which originate from the target compound introduced into the ion trap 2. As a result, at the end of the predetermined cooling period, the $[M+H]^+$-3Sia ion, which has all the sialic acids dissociated, is overwhelmingly abundant among the ions originating from the target compound and remaining in the ion trap 2, while the other ions decrease in quantity.

Thus, in the present embodiment, the gas supplier 4, which includes the gas introduction tube 41, the gas selection valve 42, the argon supply source 44 and other components for introducing argon as the cooling gas into the ion trap 2, corresponds to the non-ion-selecting fragmentation promoter in the present invention.

FIG. 6(b) is one example of the mass spectrum obtained by an actual measurement with argon as the cooling gas. As is evident in FIG. 6(b), the ion which had no sialic acid dissociated, $[M+H]^+$, was not observed in this measurement. The other three kinds of ions were observed, of which the $[M+H]^+$-3Sia ion with all the sialic acids dissociated had an extremely high intensity.

After the two mass spectra are obtained with different kinds of cooling gas, the neutral-loss analyzer 52 and the spectrum comparison processor 53 in the data processor 5 compare the peak patterns of the two mass spectra and collect information available for the assignment of the peaks (Step S3).

A specific example of the process performed by the neutral-loss analyzer 52 and the spectrum comparison processor 53 is as follows: Since the kinds of weak-bonding modifications and functional groups are limited and previously known, the mass difference due to the dissociation of one modification or functional group can also be previously known. Accordingly, the neutral-loss analyzer 52 calculates the mass-to-charge-ratio differences of a plurality of peaks located on the obtained mass spectra (i.e. the masses of neutral losses) and compares the calculated values with the masses of the known modifications and functional groups to search for a peak group, i.e. a set of peaks which originate from one compound and appear at equal mass-to-charge-ratio intervals according to whether or not dissociation has occurred or how many components have been disociated. For example, in the mass spectrum shown in FIG. 6(a), the peaks (1), (2), (3) and (4) are located at mass-to-charge-ratio intervals corresponding to the sialic acid and hence can be extracted as one set, i.e. as a peak group.

Subsequently, the spectrum comparison processor 53 determines the intensity of each of the peaks included in the peak group extracted as a result of the neutral-loss analysis. It also extracts, from the second mass spectrum, the peaks located at the same mass-to-charge ratios as the peaks included in the aforementioned peak group, and determines the intensity of each of the extracted peaks.

Table 1 shows the intensity of each peak in the peak groups obtained for the mass spectra shown in FIGS. 6(a) and 6(b). Table 2 shows the ratio of the intensity of each peak to that of the peak having the smallest mass-to-charge ratio in each of the peak groups.

TABLE 1

| | | Peak Intensity [nA] | | | |
|---|---|---|---|---|---|
| | | (4) | (3) | (2) | (1) |
| Cooling Gas | He | 24.92 | 37.97 | 34.18 | 15.01 |
| | Ar | 59.83 | 45.90 | 2.55 | 0 |

TABLE 2

| | | Peak Intensity [nA] | | | |
|---|---|---|---|---|---|
| | | (4) | (3) | (2) | (1) |
| Cooling Gas | He | 1 | 1.5 | 1.37 | 0.6 |
| | Ar | 1 | 0.77 | 0.04 | 0 |

Table 2 demonstrates that changing the cooling gas from helium to argon had the dramatic effect of decreasing the peak-intensity ratios of the [M+H]$^+$, [M+H]$^+$-Sia and [M+H]$^+$-2Sia ions with at least one sialic acid remaining, as compared to the peak intensity of the [M+H]$^+$-3Sia ion with all the sialic acids dissociated. Accordingly, the spectrum comparison processor 53 evaluates the magnitude of this change in the peak-intensity ratio, for example, by comparing it with a predetermined threshold. If that change is determined to be a significant change, the peak having the smallest mass-to-charge ratio in the peak group is determined to be the peak of an ion with all the sialic acids dissociated. In this case, it is also possible to determine that a plurality of peaks appearing at equal mass intervals in the increasing direction of the mass-to-charge ratio from the peak of the ion with all the sialic acids dissociated are a group of ions with the number of sialic acids increasing by one for each ion.

Conversely, if it is determined by the spectrum comparison processor 53 that the aforementioned change in the peak-intensity ratio is not a significant change for determining the difference in the dissociating effect, it is probable that the peak having the smallest mass-to-charge ratio in the peak group is not an ion with all the sialic acids dissociated. Accordingly, in such a case, it is possible to immediately proceed to the next process, such as a search for a peak group consisting of a different combination of peaks.

If the peak having the smallest mass-to-charge ratio in the peak group extracted from the mass spectrum obtained by using helium as the cooling gas does not have a counterpart peak at the same mass-to-charge ratio on the mass spectrum obtained by using argon as the cooling gas, it is most likely that the peak having the smallest mass-to-charge ratio in the aforementioned peak group is not a peak originating from the target compound. That is to say, the peak in question is probably a peak originating from an impurity, a peak of an ion corresponding to a different kind of molecule which was dissociated from the target compound and happened to have the same mass as the sialic acid, or a peak due to some kind of noise. Accordingly, a new peak group can be formed by excluding that peak and the previously described process based on the peak-intensity ratio can be performed for the new peak group.

After the information for determining the assignment of the peaks has been collected in the previously described manner, the peak assignment determiner 54 determines the assignment of the peaks on the mass spectra (Step S4). In other words, if a peak has been determined to have a high probability of being a peak corresponding to an ion which has originated from the target compound and from which a specific kind of modification or functional group has been partially or entirely dissociated or on which all of them remain added, the peak should be assigned, for example, to [M+H]$^+$, [M+H]$^+$-Sia, [M+H]$^+$-2Sia or [M+H]$^+$-3Sia. For any other peak which has been determined to be a peak that has not been assigned to or is unlikely to be assigned to any of those ions, the result can be given as "Assignment Unknown" or the like. Applying such rules improves the accuracy of the peak assignment, which has the effect of improving the accuracy of the identification of an unknown compound or the structural analysis of a target compound.

In addition to comparing the peak-intensity ratios to make the simple "Yes/No" determination, it is also possible, for example, to calculate a score which indicates the reliability of the possibility of the peak assignment according to the magnitude of the change in the intensity ratio which occurs when the kind of cooling gas is changed, and to output the assignment result with the scores. This allows an analysis operator to recognize the reliability of the peak assignment automatically performed with reference to the scores, and to use the information for identification or structural analysis.

Figure 4:
FIG. 4 shows a schematic structure of a phosphorylated peptide (SEQ ID NO: 2) as one example of the analysis target.

As another example of the actual measurement relating to the first embodiment, the result of a measurement performed for phosphorylated peptide having the structure shown in FIG. 4 is hereinafter described. This phosphorylated peptide is a peptide having a phosphate group (—H$_3$PO$_4$) bonded to a serine side chain. A structure formed by dissociating this phosphate group corresponds to the core structure for the target compound in the present measurement example.

Figure 7:
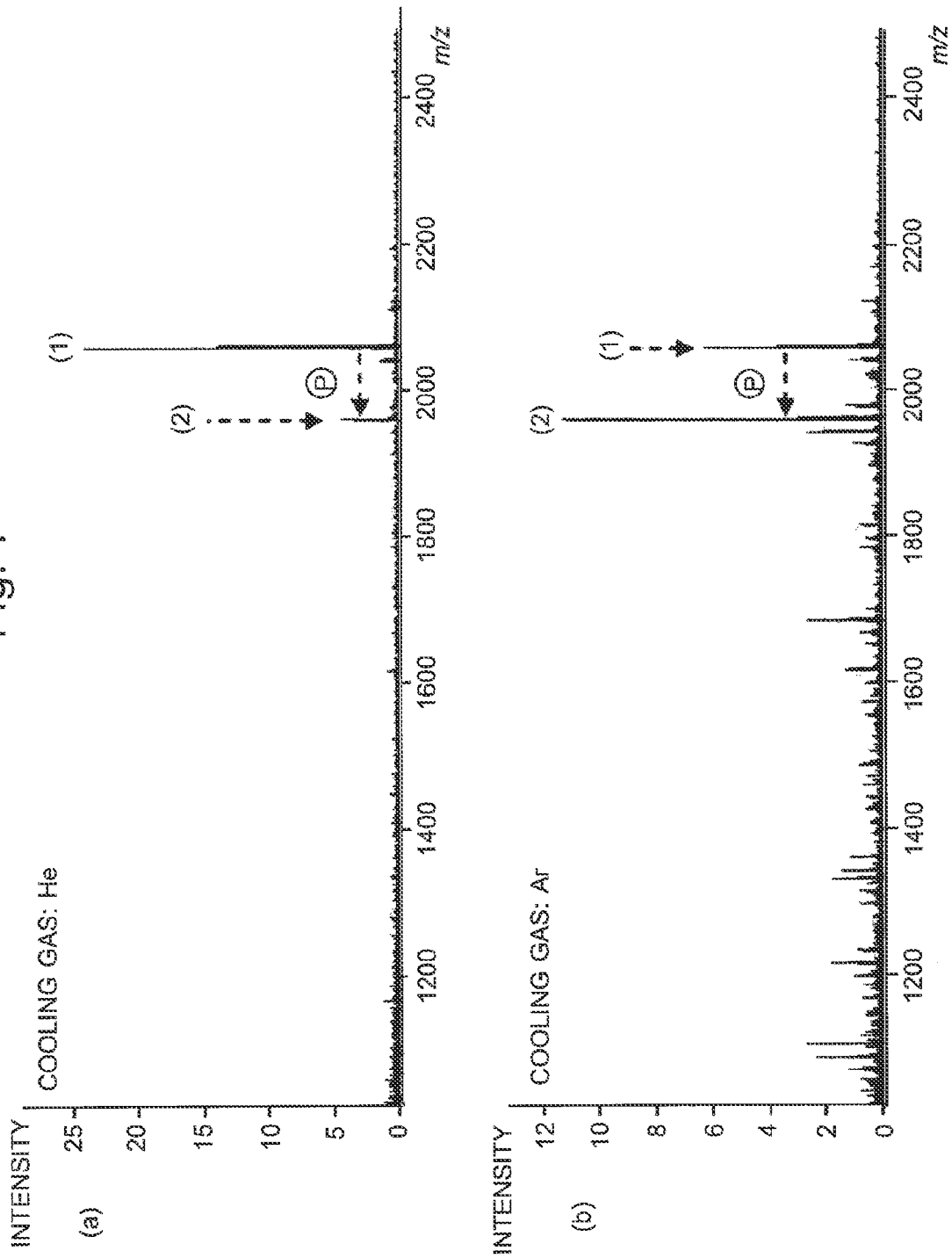
FIG. 7 shows mass spectra obtained by actual measurements of the phosphorylated peptide shown in FIG. 4.

FIG. 7(*a*) is a mass spectrum obtained by an actual measurement with helium as the cooling gas, and FIG. 7(*b*) is a mass spectrum obtained by an actual measurement with argon as the cooling gas. Similarly to the previous measurement example, DHB was used as the matrix. As can be seen in FIGS. 7(*a*) and 7(*b*), even when helium was used as the cooling gas, a [M+H]$^+$—H$_3$PO$_4$ ion formed by dissociating the phosphate acid from the proton-added ion [M+H]$^+$ was already observed along with the proton-added ion. However, the intensity of the [M+H]$^+$—H$_3$PO$_4$ ion with the phosphate acid dissociated significantly increased after the cooling gas was changed to argon. This result suggests that argon has a stronger effect of dissociating the phosphate acid than helium.

Table 3 shows the intensity of each peak in the peak groups obtained for the mass spectra shown in FIGS. 7(*a*) and 7(*b*). Table 4 shows the ratio of the intensity of each peak to that of the peak having the smallest mass-to-charge ratio in each of the peak groups.

TABLE 3

| | | Peak Intensity [nA] | |
|---|---|---|---|
| | | (2) | (1) |
| Cooling Gas | He | 4.26 | 20.58 |
| | Ar | 11.03 | 6.02 |

TABLE 4

| | | Peak Intensity [nA] | |
|---|---|---|---|
| | | (2) | (1) |
| Cooling Gas | He | 1 | 4.8 |
| | Ar | 1 | 0.5 |

Table 4 demonstrates that, also in the present example, changing the cooling gas from helium to argon had the dramatic effect of decreasing the peak-intensity ratio of the [M+H]$^+$ ion with the phosphate acid added, as compared to the peak intensity of the [M+H]$^+$—H$_3$PO$_4$ ion with the phosphate acid dissociated. Accordingly, in this case of the phosphorylated peptide, the accuracy of the assignment of the peaks originating from a target compound can be improved by comparing the peak patterns of a plurality of mass spectra obtained with different kinds of cooling gas, as in the case of the glycopeptide to which a sialylated sugar chain is added.

Figure 5:
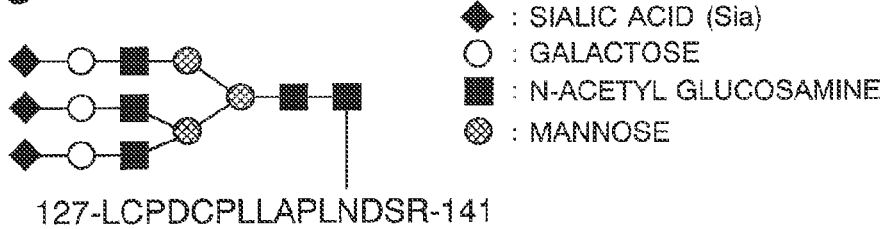
FIG. 5 shows a schematic structure of a glycopeptide (SEQ ID NO: 3) as one example of the analysis target.

As still another example of the actual measurement relating to the first embodiment, the result of a measurement performed for a glycopeptide having the structure shown in FIG. 5 is hereinafter described. This glycopeptide is a triantennary fetuine glycopeptide GP1 (bovine fetuine-GP1), which has the same sugar chain as Fetuine-GP3 shown in FIG. 3 and a different amino acid sequence. As the matrix, 3AQ/CHCA was used.

FIG. 8(a) shows one example of the mass spectrum obtained for the present sample by performing a mass spectrometry with helium as the cooling gas in an ion trap mass spectrometer. It should be noted that FIG. 8 (and FIG. 13, which will be mentioned later) is the result of accumulating 25 sets of data obtained by irradiating the sample with laser light.

In FIG. 8(a), the peak (1) corresponds to a proton-added ion [M+H]$^+$ produced by an ionization of the target compound. Due to the weak dissociation-promoting effect of helium, a portion of the sugar is dissociated during the analysis. The major ion-peak groups (2)-(5) in FIG. 8(a), which occur due to the dissociation of sugar from the target compound, respectively correspond to the [M+H]$^+$-Sia ion, the [M+H]$^+$-2Sia ion, the [M+H]$^+$-3Sia ion, and the triplet peaks characteristic of N-linked glycopeptides including a peptide ion with all the sugar dissoiated, a peptide ion with a cross-ring-cleavage of HexNAc and a HexNAc-added peptide ion. Naturally, the assignment of these peaks is unknown when the target compound remains unidentified.

FIG. 8(b) shows one example of the mass spectrum obtained by an actual measurement with argon as the cooling gas. Due to the relatively strong dissociation-promoting effect, the peak intensities of the ions corresponding to the peaks (1)-(3) in FIG. 8(a) decreased, while those of the ions corresponding to the peaks (4) and (5) increased. As shown in FIGS. 8(a) and 8(b), the mass-to-charge-ratio interval of the peaks (1)-(4) is approximately 291 Da, which corresponds to the mass that occurs as a neutral loss of the sialic acid. Therefore, for the same reason as applied to the result shown in FIGS. 6(a) and 6(b), the peaks (2)-(4) in FIG. 8(a) can be determined to have a high probability of being the ions produced within the ion trap by the dissociation of sialic acids from the [M+H]$^+$ ion which has no sialic acids dissociation. The peak group (5) can also be determined to have a high probability of being the ions newly produced from the [M+H]$^+$ ion by the dissociation-promoting effect within the ion trap, and furthermore, the mass-to-charge-ratio interval of the peaks constituting the peak group suggests that these peaks correspond to the aforementioned triplet peaks characteristic of N-linked glycopeptides.

As described thus far, by using the difference in the dissociation-promoting effect between argon and helium, it is possible to obtain information equivalent to an MS$^2$ spectrum obtained from an MS$^2$ analysis and to determine the assignment of the peaks from that information. FIG. 8(c) is an MS$^2$ spectrum obtained by an MS$^2$ analysis including a CID operation in which the [M+H]$^+$-3Sia ion peak labeled as (4) in FIG. 8(a) was used as the precursor ion. Common ion peaks can be found in both FIGS. 8(b) and 8(c) on the lower mass-to-charge ratio side of the [M+H]$^+$-3Sia ion. This fact suggests that FIG. 8(b) can be regarded as a pseudo-MS$^2$ spectrum. It can also be seen that the spectrum shown in FIG. 8(b) superbly has higher ion-peak intensities on the whole.

In the system of the previously described embodiment, helium was used as the low-mass cooling gas, and argon was used as the high-mass cooling gas. However, these are not the only possible choices for the cooling gas.

In view of the gist of the present invention, it is evidently preferable to use a plurality of cooling gases having a larger difference in the effect of dissociating weak-bonding modifications and/or functional groups. For this purpose, the use of helium as one of the gases is preferable since it has the smallest mass, and furthermore, it is easy to obtain. As the other cooling gas, krypton or xenon may also be used since they have larger masses and hence stronger dissociating effects than argon. However, using those elements is not practical due to their high cost and for other reasons. Neon, which has a smaller mass than argon, could also be used in place of argon. However, it is difficult to find an advantage of using neon since this element is more expensive than argon and has a weaker dissociating effect. In this respect, nitrogen is useful as an alternative to argon since it has a closer mass to argon, and furthermore, is inexpensive.

[Second Embodiment]

An ion trap mass spectrometer as the second embodiment of the present invention, and a characteristic mass spectrometric method performed by the mass spectrometer, are hereinafter described with reference to the attached drawings. The ion trap mass spectrometer of the second embodiment is particularly designed for the structural analysis of glycopeptides to which a weak-bonding sugar is added (concretely, N-linked glycopeptides). A difference from the first embodiment exists in the means corresponding to the non-ion-selecting fragmentation promoter in the present invention. Furthermore, the ion trap mass spectrometer of the second embodiment does not only determine the assignment of the peaks on a mass spectrum but also selects a precursor ion based on the result of the peak assignment and performs an identification and sugar-chain structural analysis of peptides constituting a glycopeptide by using a mass spectrum obtained by an MS$^2$ analysis (pseudo-MS$^3$ analysis) for that precursor ion.

Figure 9:
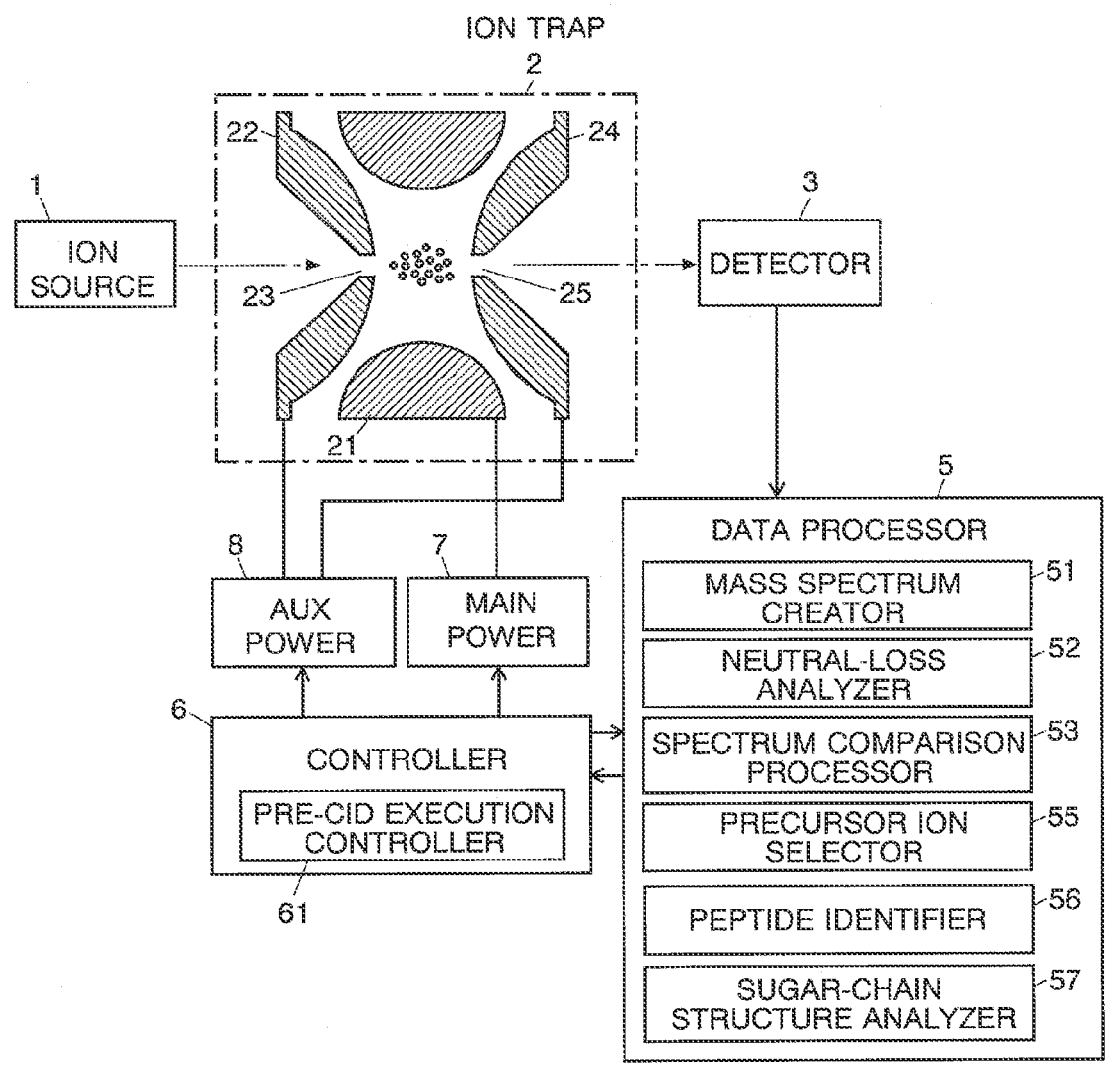
FIG. 9 is a schematic configuration diagram of an ion trap mass spectrometer as the second embodiment of the present invention.

FIG. 9 is a schematic configuration diagram of the ion trap mass spectrometer according to the second embodiment. In the system shown in FIG. 9, the components identical or corresponding to the components shown in FIG. 1 are given the same numerals. The ion source 1 and the detector 3, which are represented in a simplified form in FIG. 9, can naturally be configured as shown in FIG. 1.

As shown in FIG. 9, the controller 6 in the ion trap mass spectrometer of the second embodiment includes a pre-CID execution controller 61 as a functional block. In the normal CID operation, the selection (separation) of a precursor ion to be subjected to the CID is initially performed, and the selectively retained ion having a specific mass-to-charge ratio is fragmented in the CID process. By contrast, in the pre-CID, which corresponds to the fragmentation-promoting operation by the non-ion-selecting fragmentation promoter in the present invention, the selection of a precursor ion which precedes a significant CID is not performed; instead, a fragmentation aimed at an ion with a specific mass-to-charge ratio or ions within a specific range of mass-to-charge ratios is performed by the CID. Similarly to the normal CID, the pre-CID is performed by applying predetermined voltages from the main power source 7 and the auxiliary power source 8 to the electrodes 21, 22 and 24, respectively.

Furthermore, the data processor 5 in the ion trap mass spectrometer of the second embodiment includes a precursor ion selector 55 for selecting a precursor ion for a pseudo-MS$^3$ analysis, a peptide identifier 56 for identifying a peptide based on a mass spectrum, and a sugar-chain structure analyzer 57 for analyzing the structure of a sugar chain as functional blocks in addition to the mass spectrum creator 51, the neutral-loss analyzer 52 and the spectrum comparison processor 53.

Figure 10:
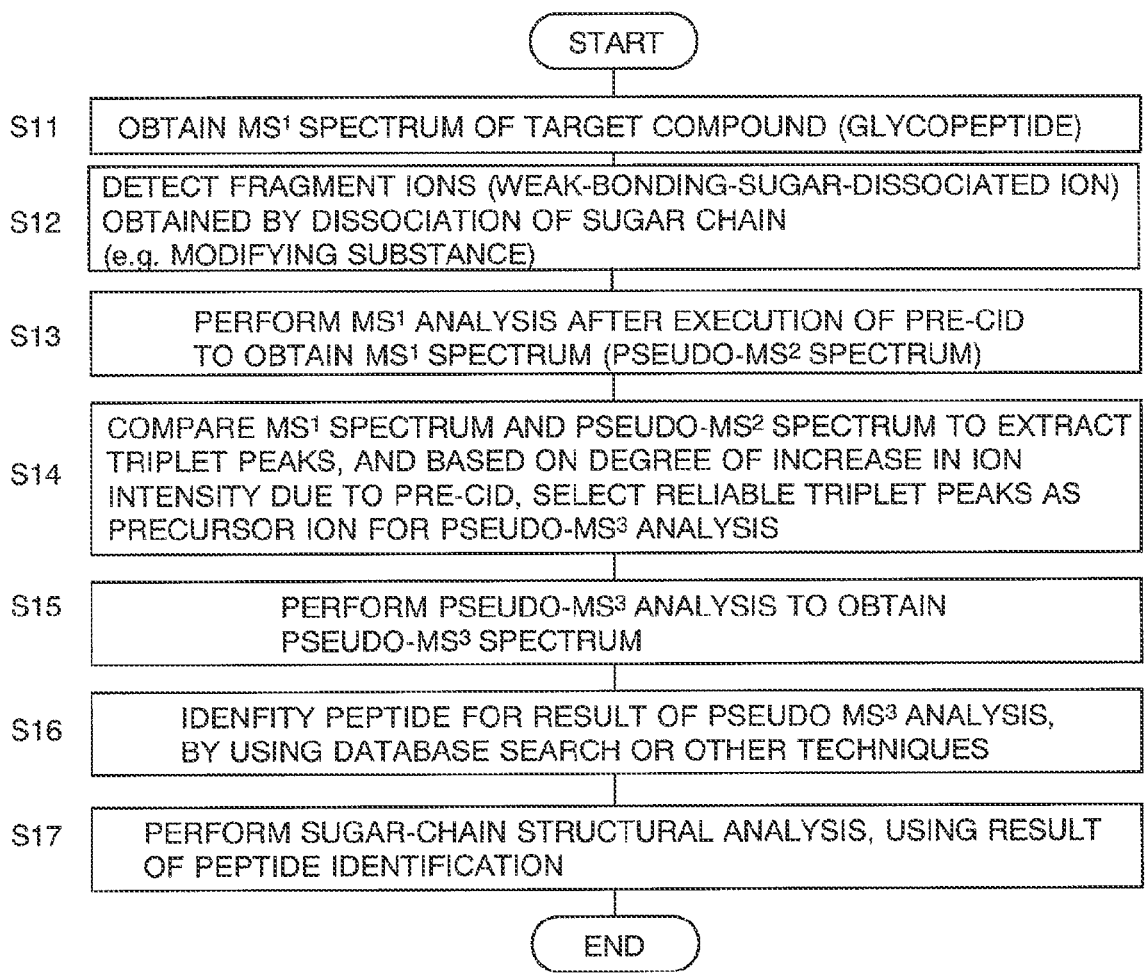
FIG. 10 is a flowchart showing the process steps of a glycopeptide structural analysis using the ion trap mass spectrometer of the second embodiment.
Figure 11:
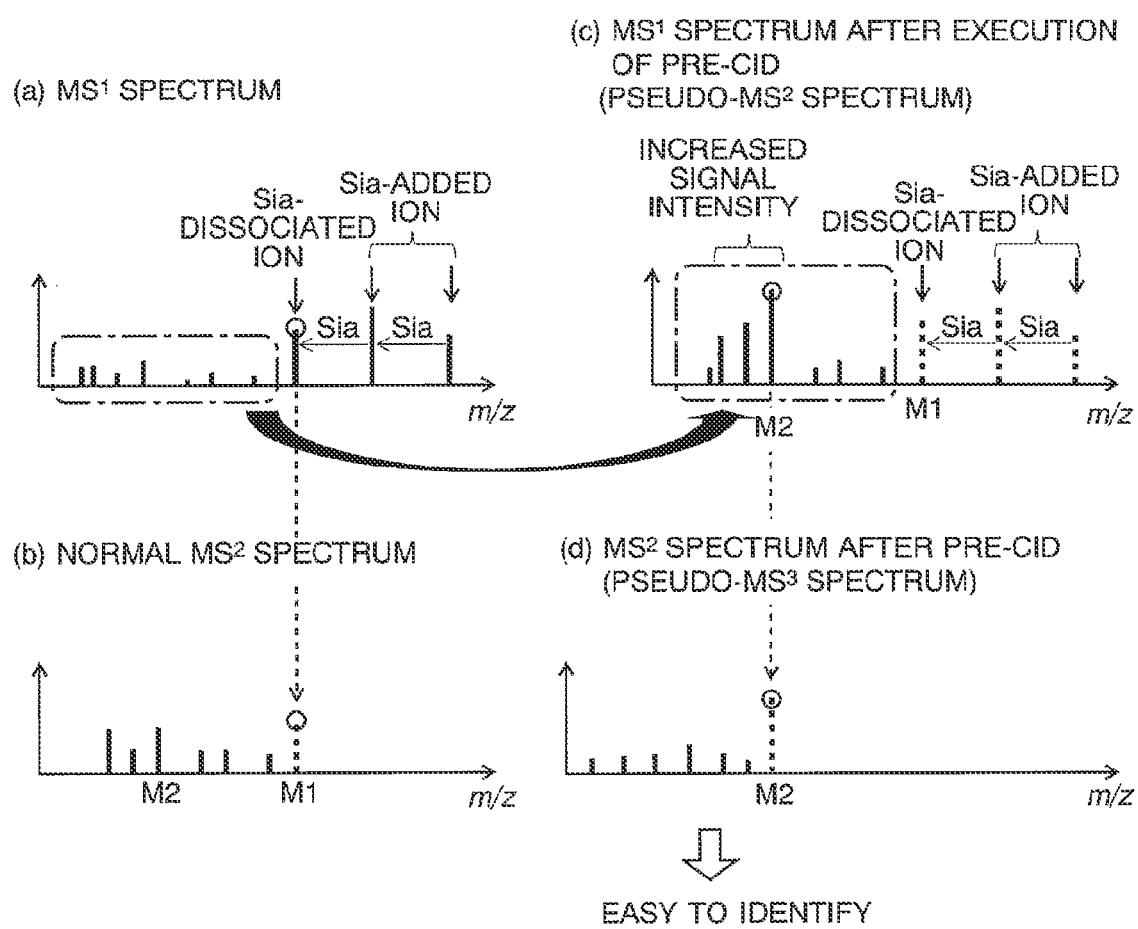
FIG. 11 shows mass spectra obtained by the ion trap mass spectrometer of the second embodiment after a pre-CID is performed and after a pseudo-$MS^2$ is performed.

One example of the controlling and processing steps for the structural analysis of a glycopeptide in the ion trap mass spectrometer of the second embodiment is hereinafter described with reference to FIGS. 10 and 11. FIG. 10 is a flowchart showing the controlling and processing steps of a glycopeptide structural analysis using the ion trap mass spectrometer of the second embodiment. FIG. 11 shows mass spectra obtained after a pre-CID is performed and after a pseudo-MS$^3$ is performed.

When an analysis is initiated under the control of the controller 6 upon request from an analysis operator, a mass spectrometry (MS$^1$ analysis) for a target compound (i.e. a glycopeptide) in a sample is performed. Based on the data obtained by this analysis, the mass spectrum creator 51 creates a mass (MS$^1$) spectrum (Step S11). This spectrum corresponds to the first mass spectrum in the present invention. For example, suppose that a mass spectrum as shown in FIG. 11(a) has been obtained.

Next, the neutral-loss analyzer 52 compares the mass-to-charge-ratio differences of the peaks (i.e. the masses of neutral losses) on the mass spectrum obtained by the MS$^1$ analysis and the masses of known sugar chains (or modifications or the like) to detect a fragment ion produced by the dissociation of a sugar chain ("weak-bonding-sugar-dissociated ion") (Step S12). This process is substantially identical to a portion of the process performed in Step S3 of the first embodiment. For example, the mass spectrum shown in FIG. 11(a) has three peaks with the mass-to-charge-ratio difference corresponding to sialic acid. Therefore, the peak having the smallest mass-to-charge ratio in those three peaks is determined to be the fragment ion with all the sugar chains dissociated.

Subsequently, for the same target compound, a pre-CID operation aimed at the weak-bonding-sugar-dissociated ion detected in Step S12 is performed to promote fragmentation of this ion, after which an MS$^1$ analysis is performed. Based on the data obtained by this MS$^1$ analysis, the mass spectrum creator 51 creates a mass spectrum (Step S13). A weak-bonding-sugar-added ion may also be included as the target of the pre-CID in addition to the weak-bonding-sugar-dissoicated ion. That is to say, in the example of FIG. 11, an ion which with a mass-to-charge ratio m/z of M1, from which the sialic acids (Sia) have been dissociated, is designated as the target of the pre-CID, or an ion which has one or more sialic acids added (not dissociated) and has a mass-to-charge ratio m/z of M1+Sia or M1+2Sia is additionally designated as the target of the pre-CID. Although the mass spectrum obtained in Step S13 is an MS$^1$ spectrum, it can be regarded as a pseudo-MS$^2$ spectrum obtained by a pseudo-MS$^2$ analysis since this mass spectrum is obtained after the fragmentation of the ions originating from the target compound is promoted by the pre-CID.

FIG. 11(c) is a mass (pseudo-MS$^2$) spectrum obtained under the condition that the pre-CID was performed with both the sialic-acid-dessociated and sialic-acid-added ions designated as the targets. The pre-CID promotes fragmentation of the sialic-acid-dissociated and sialic-acid-added ions, making the peaks of these ions barely noticeable while increasing the intensities of the fragment ions. Unlike the normal CID, the pre-CID involves no selection of a precursor ion. Therefore, the amount of ions designated as the target is large enough, and the fragment ions generated from those ions have adequately high intensities.

Subsequently, the neutral-loss analyzer 52 examines the mass-to-charge-ratio differences of the peaks detected on the pseudo-MS$^2$ spectrum and extracts a candidate of the triplet peaks (i.e. a peptide ion with all the sugar dissociated, peptide ion with a cross-ring cleavage of HexNAc residue, and a HexNAc-added peptide ion) which are characteristic of N-linked glycopeptides. In general, a plurality of candidates of the triplet peaks will be extracted when only the mass-to-charge-ratio difference is used for determination. Then, the spectrum comparison processor 53 compares each peak included in the extracted triplet-peak candidates on the pseudo-MS$^2$ spectrum to the peak having same mass-to-charge ratio on the MS$^1$ spectrum obtained in Step S11, and estimates that the peak which has shown the largest increase in the ion intensity as a result of the pre-CID is a reliable candidate of the triplet peaks. Then, the precursor ion selector 55 selects the ions constituting the triplet peaks whose assignment has been determined with high reliability as a precursor ion for a pseudo-MS$^3$ analysis (Step S14).

Figure 12:
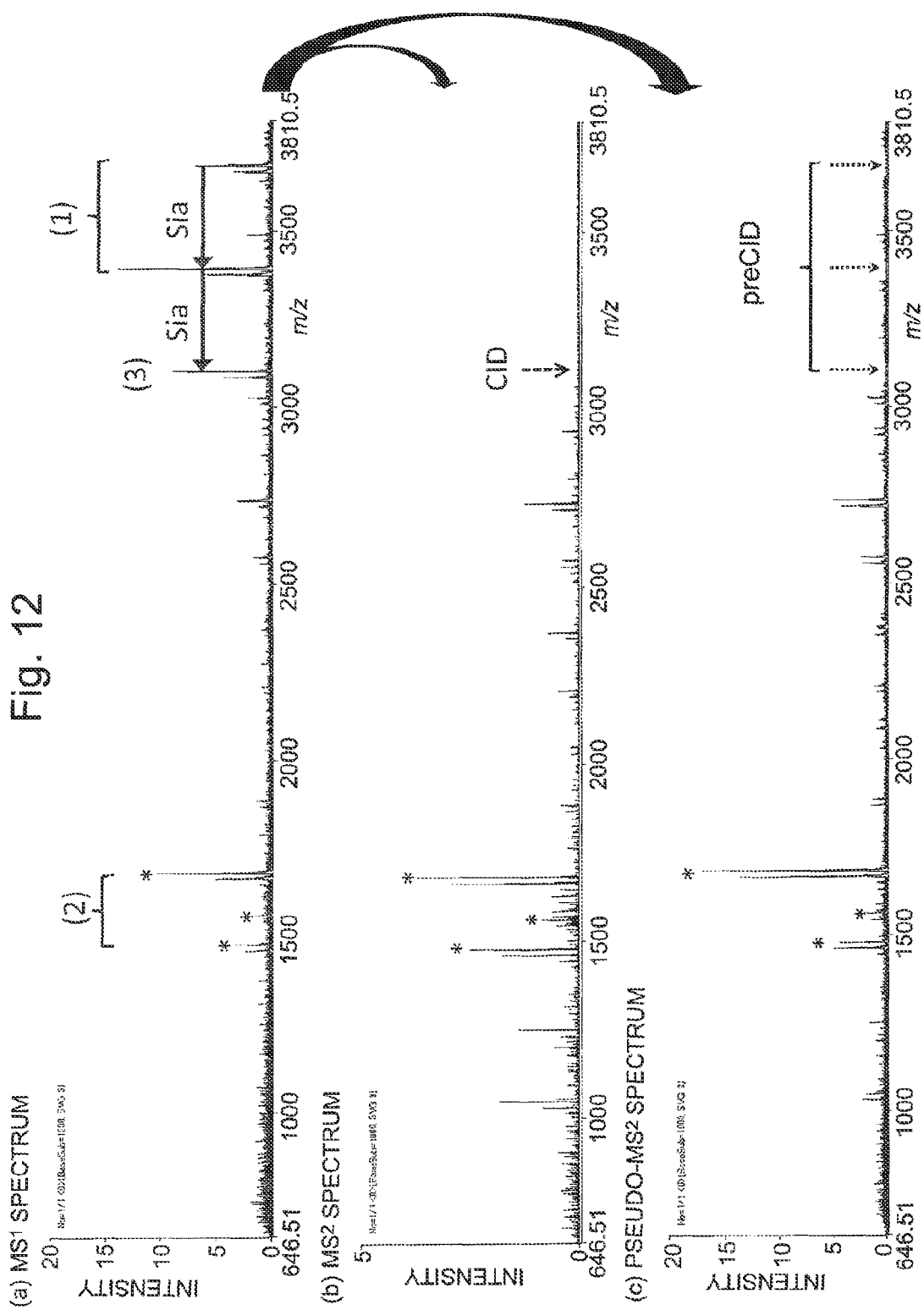
FIG. 12 shows one example of the actual measurement in which the amount of ions of the triplet peaks increased as a result of the pre-CID performed in the ion trap mass spectrometer of the second embodiment.

FIG. 12 shows an example of an actual measurement in which the ion intensities of the triplet peaks characteristic of an N-linked glycopeptide increased as a result of a pre-CID. The shown mass spectra were obtained from a bi-antennary glycopeptide of transferrin, where (a) is an MS$^1$ spectrum, (b) is a normal MS$^2$ spectrum, and (c) is a pseudo-MS$^2$ spectrum obtained by an MS$^1$ analysis after the pre-CID. Each of them shows a result obtained by accumulating signals 20 times under the same accumulation number condition. A "normal" MS$^2$ spectrum is a mass spectrum obtained by selecting a weak-bonding-sugar-dissociated ion as a precursor ion, performing a CID process using that precursor ion, and performing a mass spectrometry of the product ions produced by the CID, as shown in FIG. 11(b).

If a peak formed by a fragment ion is observed on the normal MS$^1$ spectrum shown in FIG. 12(a), it is difficult to determine whether that peak has resulted from the dissociation of sugar within the ion trap 2 or was already present even before ions were introduced into the ion trap 2 (which can typically occur due to in-source decay). However, it is reasonable to consider that an ion whose intensity has increased as a result of the pre-CID performed in the ion trap 2 is the product of the dissociation of sugar within the ion trap 2.

This could actually be confirmed for the example shown in FIG. 12: When a pseudo-MS$^2$ analysis including a pre-CID process with the sialic-acid-added ion (1) and the sialic-acid-dissociated ion (3) shown in FIG. 12(a) as the target was performed, the thereby obtained pseudo-MS$^2$ spectrum (FIG. 12(c)) showed an increase in the ion intensity of the triplet peaks recognized on the MS$^1$ spectrum (labeled as (2) in FIG. 12(a)). It can also be confirmed that, as compared to the MS$^2$ spectrum shown in FIG. 12(b) which was obtained by using the sialic-acid-dissociated ion labeled as (3) in FIG. 12(a) as the precursor ion, the pseudo-MS$^2$ spectrum superbly has higher ion intensities on the whole. This is similar to the comparison result of FIGS. 8(b) and 8(c) described earlier as an example of the actual measurement of the first embodiment.

After the triplet peaks have been extracted in Step S14, a protein database search may be conducted for peak information collected from the pseudo-MS$^2$ spectrum, with the mass-to-charge ratios corresponding to the triplet peaks set as one search key which specifies the mass-to-charge ratio of the precursor ion, and either HexNAc or cross-ring cleavage of HexNAc residue set as another search key which specifies a modifying condition. As a result of this database search, if the peptide has been identified with high reliability, it is no longer necessary to perform a pseudo-MS$^3$ analysis and the following processes of Steps S15 and S16 can be omitted.

As a result of the protein database search, if a peptide has been found with a degree of reliability (homology) equal to or higher than a certain level, the triplet peaks used for that search can be regarded as an even more reliable candidate of the triplet-peaks. It is also possible to conclude that the assignment of triplet peaks has been determined with high reliability if a HexNAc-added peptide has ranked first (topmost) as a result of the protein database search in which the peak having the largest mass-to-charge ratio in the triplet peaks is specified as the precursor ion, or if a peptide ion with a cross-ring cleavage of HexNAc has ranked first as a result of the protein database search in which the peak having the second largest mass-to-charge ratio in the triplet peaks is specified as the precursor ion. That is to say, it is possible to use the protein database search for the determination of the reliability of the triplet peaks only, and not for the identification of a peptide.

After a precursor ion is selected in Step S14, the controller 6 receives an instruction and conducts an $MS^2$ analysis for that precursor ion. Based on the data obtained by the analysis, the mass spectrum data creator 51 creates a mass spectrum. This mass spectrum is a pseudo-$MS^3$ spectrum obtained by a pseudo-$MS^3$ analysis in which CID is virtually performed two times (Step S15). FIG. 11(d) is a pseudo-$MS^3$ spectrum obtained by a pseudo-$MS^3$ analysis in which one of the triplet peaks extracted on the pseudo-$MS^2$ spectrum shown in FIG. 11(c) is designated as the precursor ion.

After the pseudo-$MS^3$ spectrum is obtained, the peptide identifier 56 identifies the peptide by conducting a protein database search for peak information collected from the pseudo-$MS^3$ spectrum (Step S16). As already noted, the pseudo-$MS^3$ analysis involves a smaller number of precursor-ion selecting operations than the normal $MS^3$ analysis, and accordingly, the fragment ions have higher intensities on the whole. Therefore, the protein database search based on the peak information collected from the pseudo-$MS^3$ spectrum improves the accuracy of the peptide identification and reduces incorrect identification or overlooking of the peptide.

If the peptide is identified in Step S16, the sugar-chain structure analyzer 57 selects, as the precursor ion for an $MS^2$ analysis, a weak-bonding-sugar-added ion (or weak-bonding-sugar-dissociated ion) observed on the $MS^1$ spectrum, conducts an $MS^2$ analysis, and performs a sugar-chain structural analysis based on the obtained $MS^2$ spectrum (Step S17). For the sugar-chain structural analysis, commonly known methods can be used, such as the de-novo sequencing or sugar-chain structure database search. In the case of performing the sugar-chain structure database search, the peptide identified in Step S16 can be provided as structural information. An example of the sugar-chain structure database search software that can be used when the kind of peptide is known is the one introduced in the aforementioned document (*Nature Protocols*).

As another example of the actual measurement relating to the second embodiment, the result of a measurement performed for a glycopeptide having the structure shown in FIG. 5 is hereinafter described. FIG. 13(a) is an $MS^1$ spectrum obtained by performing a pre-CID in which ion peaks (1)-(4) observed on the mass spectrum shown in FIG. 8(a) were selected as the target. As compared to the result shown in FIG. 8(a) which was obtained without performing the pre-CID, the intensities of the ion peaks on the lower mass-to-charge ratio side of the peak (4) (e.g. the intensities of the triplet peaks) generally increased. It is reasonable to consider that those ions with increased intensities are the products of the dissociation of sugar within the ion trap 2. That is to say, it can be understood that the pre-CID has a strong dissociation-promoting effect similar to the previously described case of the first embodiment in which argon was used as the cooling gas.

As described thus far, with the ion trap mass spectrometer of the second embodiment, it is possible to improve the reliability of the assignment of the triplet peaks characteristic of N-linked glycopeptides by using a pre-CID, which is one form of the non-ion-selecting fragmentation promoter in the present invention, and to perform an identification of peptides or structural analysis of sugar chains with high accuracy based on the triplet peaks.

In the second embodiment, the fragmentation promotion using the difference in the kind of cooling gas described in the first embodiment may be performed in place of, or in addition to, the pre-CID. Similarly, in the first embodiment, the pre-CID may be performed in place of, or in addition to, the fragmentation promotion using the difference in the kind of cooling gas.

FIG. 14 is a flowchart showing the steps of a process in which argon is used as the cooling gas in the glycopeptide structural analysis using the ion trap mass spectrometer of the second embodiment. The flowchart shown in FIG. 14 is almost identical to the one shown in FIG. 10; the difference exists in that helium is used as the cooling gas in Step S11B, which corresponds to Step S11 in FIG. 10, and that argon is used as the cooling gas in Step S13B, which corresponds to Step S13 in FIG. 10. That is to say, the dissociation of sugar chains is promoted by using argon as the cooling gas as well as by performing the pre-CID.

An example of an actual measurement in which argon was used as the cooling gas and the pre-CID was also performed is hereinafter described. FIG. 13(b) is an $MS^1$ spectrum obtained by using argon as the cooling gas and by performing a pre-CID with the ion peaks (1)-(4) in FIG. 8(a) as the target. It can be seen that, as compared to FIG. 8(a), the intensities of the ion peaks on the lower mass-to-charge ratio side of the peak (4) increased on the whole. It can also be recognized that the intensities of the triplet peaks increased to be higher than any of the two cases where argon was used as the cooling gas and no pre-CID was performed (FIG. 8(b)) or where helium was used as the cooling gas and the pre-CID was performed (FIG. 13(a)). These results demonstrate that the combination of the use of argon or similar cooling gas having a strong dissociation-promoting effect as the cooling gas and the execution of a pre-CID is effective for improving the accuracy of the assignment of the peaks, and furthermore, for improving the accuracy of identification of a compound based on the result of a pseudo-$MS^3$ analysis using the assigned peaks as a precursor ion.

Although a digital ion trap, which is driven by a rectangular voltage, is used in the ion trap mass spectrometer of any of the previous embodiments, it is also possible to use a general type of ion trap driven by a sinusoidal voltage. The ion trap does not need to be a three-dimensional quadrupole ion trap, but it may be a linear ion trap.

It should be noted that any of the previous embodiments is a mere example of the present invention, and any change, modification, addition or the like appropriately made within the spirit of the present invention will naturally fall within the scope of claims of the present patent application.

EXPLANATION OF NUMERALS

1 . . . Ion Source
11 . . . Laser Irradiation Unit
12 . . . Sample Plate
13 . . . Aperture
14 . . . Ion Lens
2 . . . Ion Trap
21 . . . Ring Electrode
22 . . . Entrance End-Cap Electrode
23 . . . Ion Injection Hole
24 . . . Exit End-Cap Electrode
25 . . . Ion Ejection Hole
3 . . . Detector
31 . . . Conversion Dynode
32 . . . Secondary Electron Multiplier
4 . . . Gas Supplier 41 . . . Gas Introduction Tube
42 . . . Gas Selection Valve
43 . . . Helium Supply Source
44 . . . Argon Supply Source
5 . . . Data Processor
51 . . . Mass Spectrum Creator
52 . . . Neutral-Loss Analyzer
53 . . . Spectrum Comparison Processor
54 . . . Peak Assignment Determiner
55 . . . Precursor Ion Selector
56 . . . Peptide Identifier
57 . . . Sugar-Chain Structure Analyzer
6 . . . Controller
61 . . . Pre-CID Execution Controller
7 . . . Main Power Source
8 . . . Auxiliary Power Source

The invention claimed is:

1. A mass spectrometer for analyzing a target compound to which one or more weak-bonding substances are bonded, comprising:
   a mass analyzer for performing a mass spectrometry of ions originating from the target compound which captures ions to be analyzed in an inner space of an ion trap and subjects the ions in the inner space of the ion trap to a mass spectrometry by the ion trap, or by an external mass analyzer after being ejected from the ion trap;
   a detector for detecting the ions separated by the mass analyzer according to their mass-to-charge ratios, the mass spectrometer comprising:
   a) a gas-selecting supplier for selectively introducing, into the ion trap, either a first inert gas or a second inert gas having a stronger effect to dissociate the weak-bonding substance from the target compound than the first inert gas as a cooling gas;
   b) a controller performing
      a first analysis for obtaining a first mass spectrum by cooling ions originating from the target compound with the first inert gas from the gas-selecting supplier without promoting fragmentation of the ions and performing a mass spectrometry of the ions originating from the target compound by using the mass analyzer and
      a second analysis for obtaining a second mass spectrum by cooling ions originating from the target compound with the second inert gas from the gas-selecting supplier with promoting fragmentation of the ions and performing a mass spectrometry of the ions originating from the target compound by using the mass analyzer without an ion-selecting operation; and
   c) a data processor for determining an assignment of a peak originating from the target compound by comparing a peak pattern of the first mass spectrum with a peak pattern of the second mass spectrum and makes at least a comparison of intensities of peaks at the same mass-to-charge ratio or a comparison of the intensity ratio of a plurality of peaks having a predetermined mass-to-charge-ratio difference on one of the mass spectra so as to locate a peak corresponding to a core structure of the target compound from which all the weak-bonding substances have been dissociated.

2. The mass spectrometer according to claim 1, wherein: the first inert gas is helium, and the second inert gas is nitrogen, neon, argon, krypton, xenon or a mixture of two or more of these gases.

3. The mass spectrometer according to claim 1, wherein: in the second analysis, the controller further performs a collision-induced dissociating operation for ions originated from the target compound and captured in the ion trap without an precursor ion selecting operation.

4. The mass spectrometer according to claim 1, wherein: the weak-bonding substances are at least one selected from a group including sialic acid, sulfate group, and phosphate group.

5. A mass spectrometric method for analyzing a target compound to which one or more weak-bonding substances are bonded, using a mass spectrometer including a mass analyzer for performing a mass spectrometry of ions originating from the target compound in which ions to be analyzed are temporarily captured in an inner space of an ion trap and then subjected to a mass spectrometry by the ion trap, or by an external mass analyzer after being ejected from the ion trap and a detector for detecting the ions separated by the mass analyzer according to their mass-to-charge ratios, the mass spectrometric method comprising:
 a) a first analysis execution step in which a first mass spectrum is obtained by cooling ions originating from the target compound and captured in the inner space of the ion trap with a first inert gas, and performing a mass spectrometry of the ions originating from the target compound by using the mass analyzer;
 b) a second analysis execution step in which a second mass spectrum is obtained by cooling ions originating from the target compound and captured in the inner space of the ion trap with a second inert gas having a stronger effect to dissociate the weak-bonding substance from the target compound than the first inert gas with promoting fragmentation of the ions, and performing a mass spectrometry of the ions originating from the target compound by using the mass analyzer without an ion-selecting operation; and
 c) a data-processing step in which an assignment of a peak originating from the target compound is determined by a peak pattern of the first mass spectrum with a peak pattern of the second mass spectrum and makes at least a comparison of intensities of peaks at the same mass-to-charge ratio or a comparison of the intensity ratio of a plurality of peaks having a predetermined mass-to-charge-ratio difference on one of the mass spectra so as to locate a peak corresponding to a core structure of the target compound from which all the weak-bonding substances have been dissociated.

6. The mass spectrometric method according to claim 5, wherein: the weak-bonding substances are at least one selected from a group including sialic acid, sulfate group, and phosphate group.

7. A mass spectrometer for analyzing an N-linked glycopeptide target compound, comprising:
 a mass analyzer for performing a mass spectrometry of ions originating from the target compound which captures ions to be analyzed in an inner space of an ion trap and subjects the ions in the inner space of the ion trap to a mass spectrometry by the ion trap, or by an external mass analyzer after being ejected from the ion trap;
 a detector for detecting the ions separated by the mass analyzer according to their mass-to-charge ratios;
 a) a pre-CID execution controller performing
  a first analysis for obtaining a first mass spectrum by performing a mass spectrometry of the ions originating from the target compound by using the mass analyzer and
  a second analysis for obtaining a second mass spectrum by performing a mass spectrometry of the ions originating from the target compound by using the mass analyzer after performing a collision-induced dissociating operation for ions originated from the target compound and captured in the inner space of the ion trap without a precursor ion selecting operation and;
 b) a data processor for extracting triplet peaks characteristic of N-linked glycopeptides by comparing the first mass spectrum and the second mass spectrum;
 c) a pseudo-$MS^3$ analysis controller for performing an $MS^2$ analysis using the triplet peaks extracted by the data processor as a precursor ion, as a pseudo-$MS^3$ analysis for the ions originating from the target compound; and
 d) a peptide identifier for identifying a peptide constituting the target compound based on a mass spectrum obtained by the pseudo-$MS^3$ analysis.

8. The mass spectrometer according to claim 7, further comprising:
 e) a cooling gas supplier for introducing, into the ion trap, a cooling gas having an effect to dissociate a weak-bonding substance from the target compound; wherein the pre-CID execution controller performs the second analysis with cooling ions originating from the target compound with the cooling gas from the cooling gas supplier.

9. A mass spectrometric method for analyzing an N-linked glycopeptide target compound, using a mass spectrometer including a mass analyzer for performing a mass spectrometry of ions originating from the target compound in which ions to be analyzed are temporarily captured in an inner space of an ion trap and then subjected to a mass spectrometry by the ion trap, or by an external mass analyzer after being ejected from the ion trap and a detector for detecting the ions separated by the mass analyzer according to their mass-to-charge ratios, the mass spectrometric method comprising:
 a) a first analysis execution step in which a first mass spectrum is obtained by performing a mass spectrometry of the ions originating from the target compound by using the mass analyzer;
 b) a second analysis execution step in which a second mass spectrum is obtained by performing a mass spectrometry of the ions originating from the target compound by using the mass analyzer after performing a collision-induced dissociating operation in which fragmentation of the ions captured in the inner space of the ion trap is promoted without a precursor ion selecting operation; and
 c) a data-processing step in which triplet peaks characteristic of N-linked glycopeptides are extracted by comparing the first mass spectrum and the second mass spectrum;
 d) a pseudo-$MS^3$ analysis step in which performing an $MS^2$ analysis is performed by using the triplet peaks extracted by the data processor as a precursor ion, as a pseudo-$MS^3$ analysis for the ions originating from the target compound; and e) a peptide identifying step in which a peptide constituting the target compound is identified based on a mass spectrum obtained by the pseudo-$MS^3$ analysis.

* * * * *